US009931207B2

(12) United States Patent
Oba et al.

(10) Patent No.: US 9,931,207 B2
(45) Date of Patent: Apr. 3, 2018

(54) METHODS OF IMPLANTING A HEART VALVE AT AN AORTIC ANNULUS

(71) Applicant: Edwards Lifesciences Corporation, Irvine, CA (US)

(72) Inventors: Travis Oba, Yorba Linda, CA (US); Rafael Pintor, Mission Viejo, CA (US); Louis A. Campbell, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/001,114

(22) Filed: Jan. 19, 2016

(65) Prior Publication Data

US 2016/0128829 A1 May 12, 2016

Related U.S. Application Data

(62) Division of application No. 12/716,961, filed on Mar. 3, 2010, now Pat. No. 9,248,016.

(Continued)

(51) Int. Cl.
*A61F 2/24* (2006.01)

(52) U.S. Cl.
CPC ............ *A61F 2/243* (2013.01); *A61F 2/2418* (2013.01); *A61F 2/2427* (2013.01); *A61F 2/2433* (2013.01); *A61F 2220/005* (2013.01); *A61F 2220/0016* (2013.01); *A61F 2220/0075* (2013.01); *A61F 2220/0083* (2013.01); *A61F 2230/008* (2013.01); *A61F 2230/0054* (2013.01); *A61F 2250/0063* (2013.01);

(Continued)

(58) Field of Classification Search
CPC ...... A61F 2/234–2/2433; A61F 2/2418; A61F 2250/0063

See application file for complete search history.

(56) References Cited

U.S. PATENT DOCUMENTS 3,143,742 A 8/1964 Cromie
3,320,972 A 5/1967 High et al.
(Continued)

FOREIGN PATENT DOCUMENTS

EP 0125393 A1 11/1984
EP 0143246 A2 6/1985
(Continued)

*Primary Examiner* — Christopher D Prone
(74) *Attorney, Agent, or Firm* — Guy Cumberbatch; Pui Tong Ho

(57) ABSTRACT

An exemplary two-stage prosthetic heart valve system has a radially expandable base stent implanted within a native valve annulus. The two-stage heart valve system also has a valve component that is delivered to and mounted within the base stent in a separate or sequential operation after the base stent has been anchored within the annulus. The valve component in certain embodiments comprises a hybrid valve component that includes a conventional, non-expandable surgical valve that is modified to include an expandable coupling stent that can be expanded to engage the inner surface of the base stent, thereby anchoring the valve component to the base stent. In its expanded configuration, the outflow end portion base stent has tri-lobular shape that closely conforms to the shape of the aortic root and a support ring of the prosthetic valve that is mounted within the base stent.

20 Claims, 19 Drawing Sheets

Related U.S. Application Data

(60) Provisional application No. 61/165,455, filed on Mar. 31, 2009.

(52) U.S. Cl.
CPC ............... *A61F 2250/0097* (2013.01); *A61F 2250/0098* (2013.01)

(56) References Cited

U.S. PATENT DOCUMENTS

| | | | |
|---|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,976,155 A | 11/1999 | Foreman et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |

(56) References Cited

U.S. PATENT DOCUMENTS

| | | |
|---|---|---|
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,790,229 B1 | 9/2004 | Berreklouw |
| 6,790,230 B2 | 9/2004 | Beyersdorf et al. |
| 6,805,111 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,998,151 B2 | 8/2011 | St. Goar et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Lakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0271172 A1 | 11/2006 | Tehrani |
| 2006/0271175 A1 | 11/2006 | Woolfson et al. |
| 2006/0276888 A1 | 12/2006 | Lee et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |

(56) References Cited

U.S. PATENT DOCUMENTS

| | | |
|---|---|---|
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0004688 A1 | 1/2008 | Spenser et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0275540 A1 | 11/2008 | Wen |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

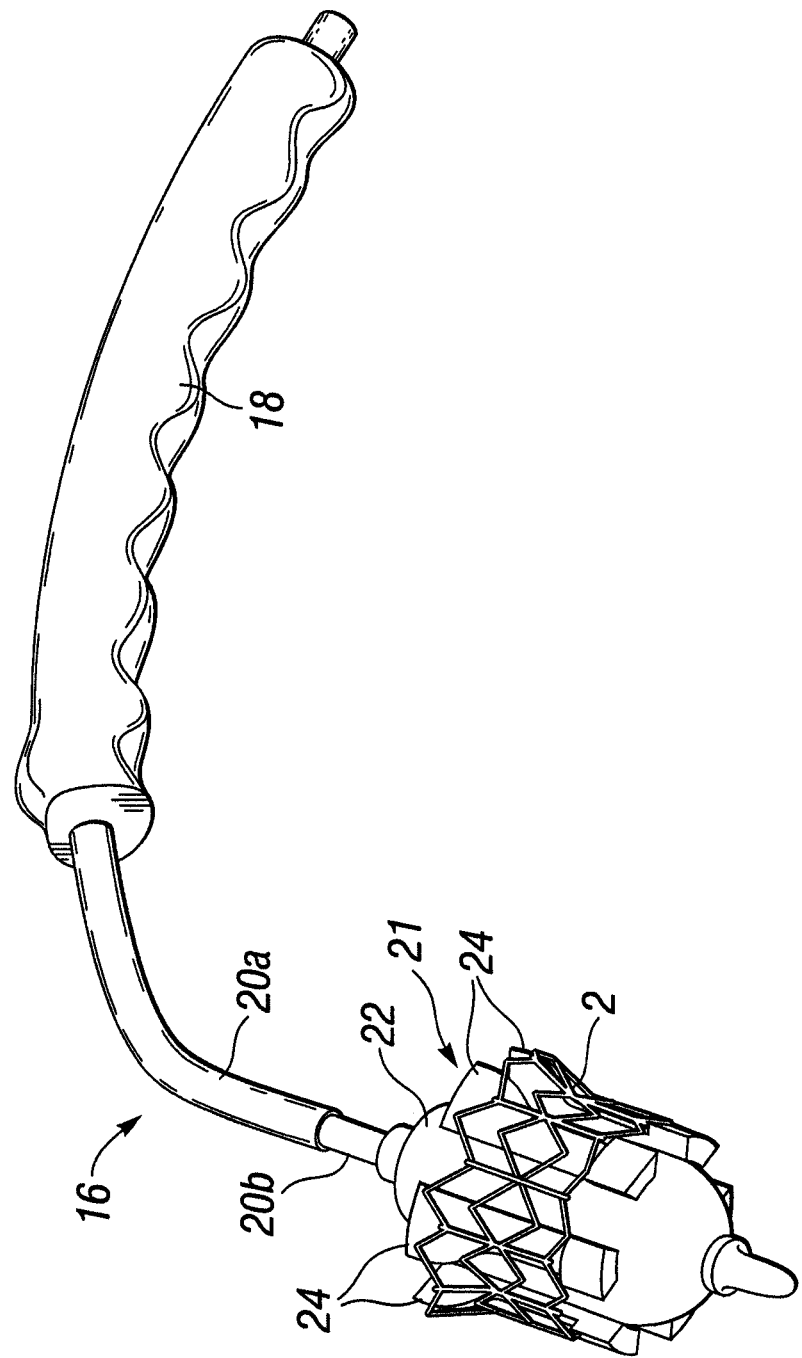

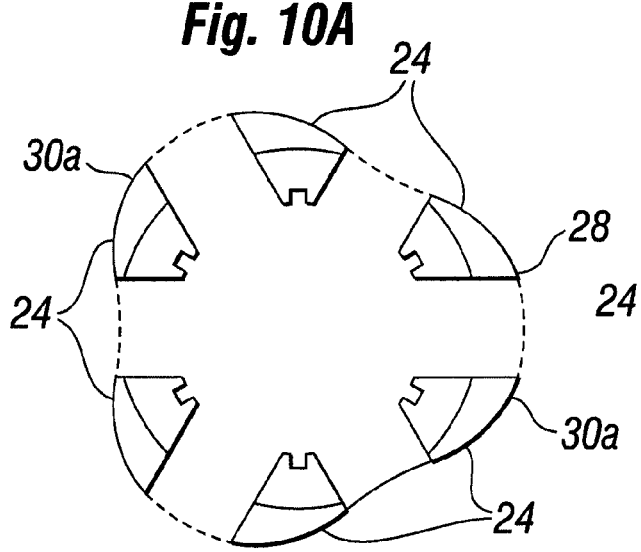
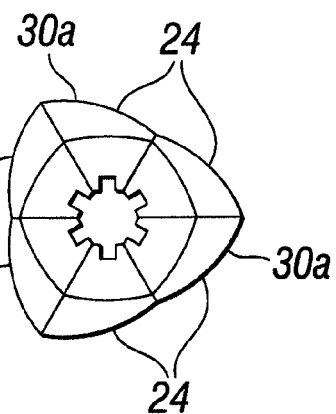
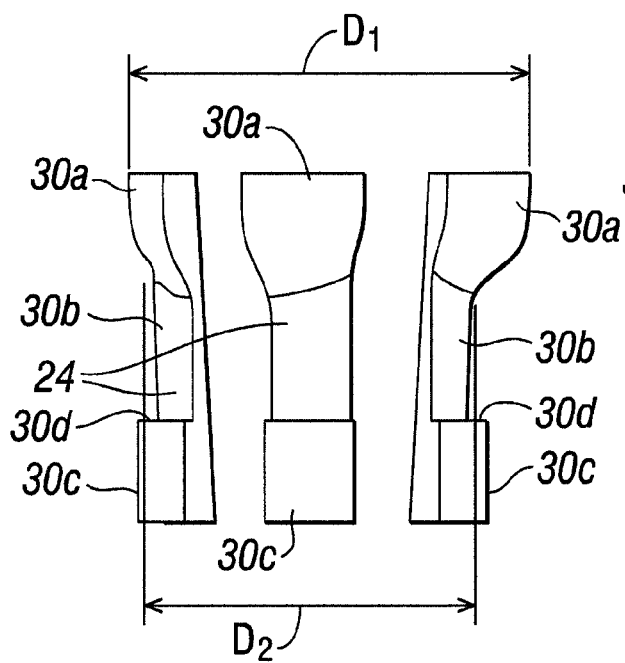
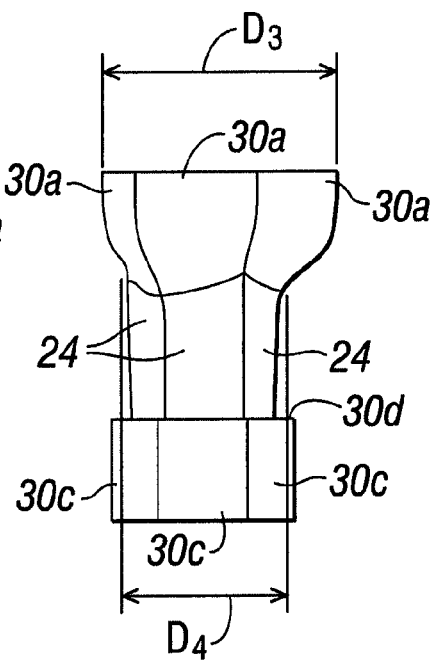

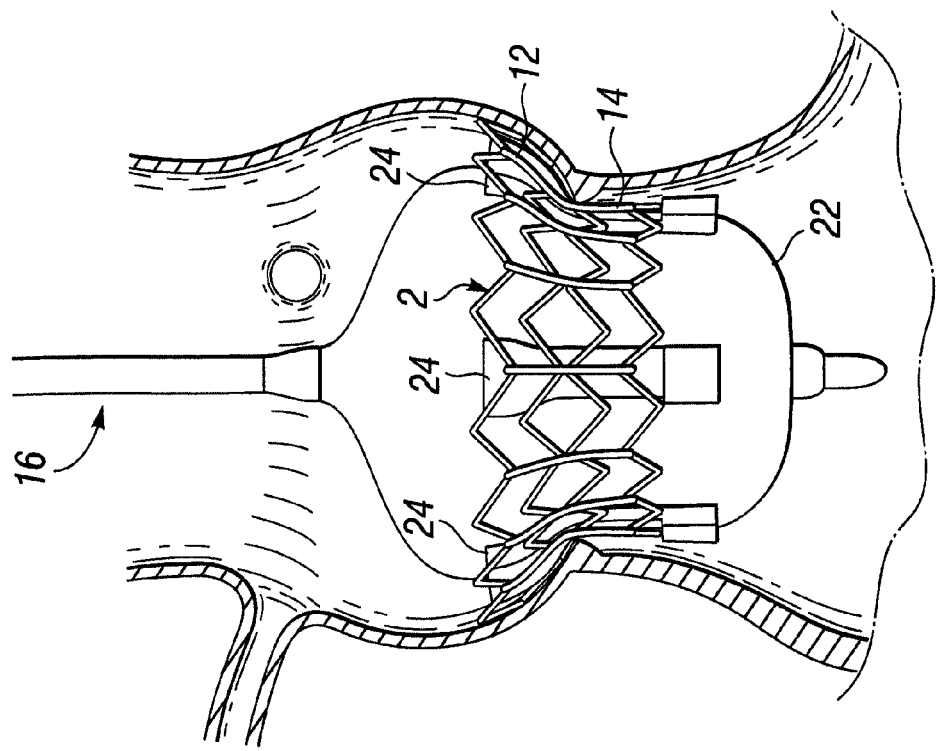
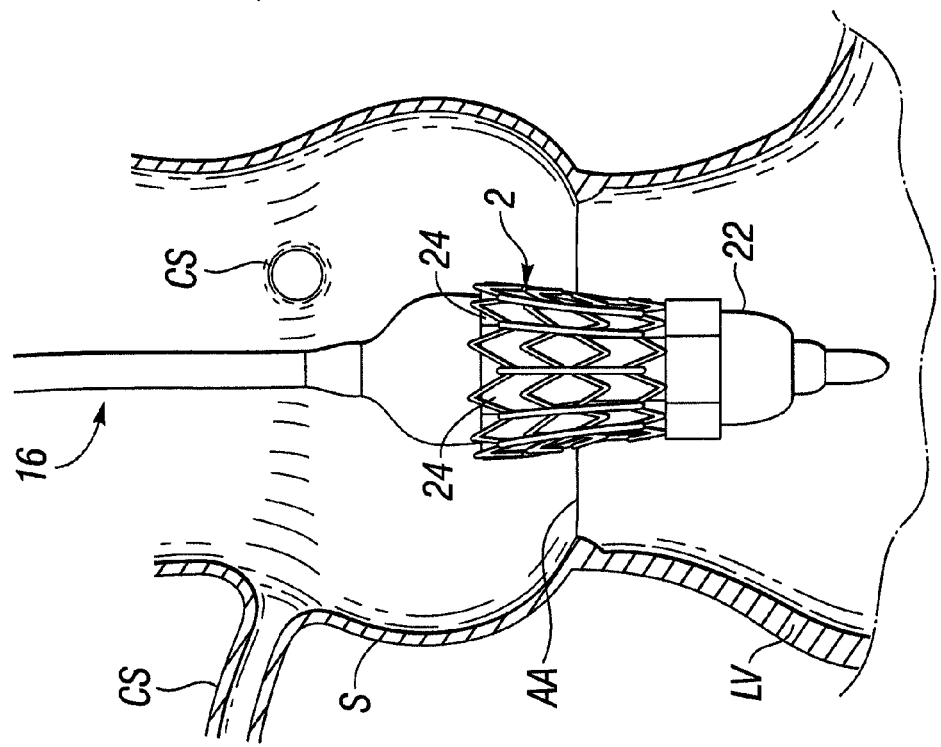

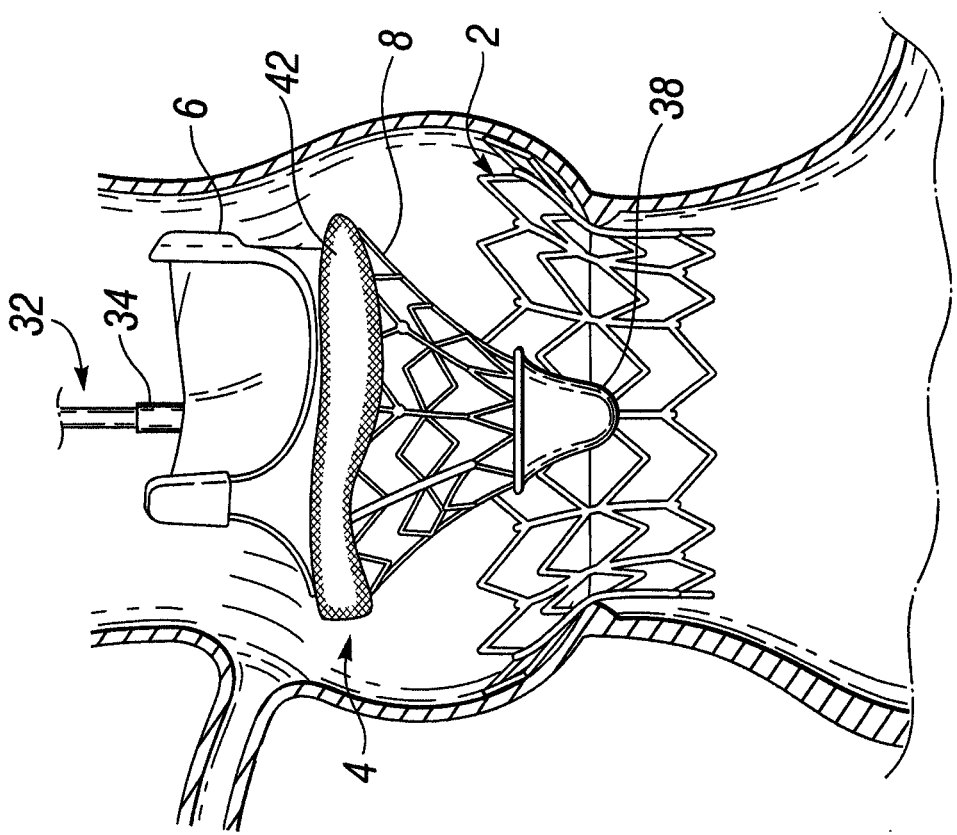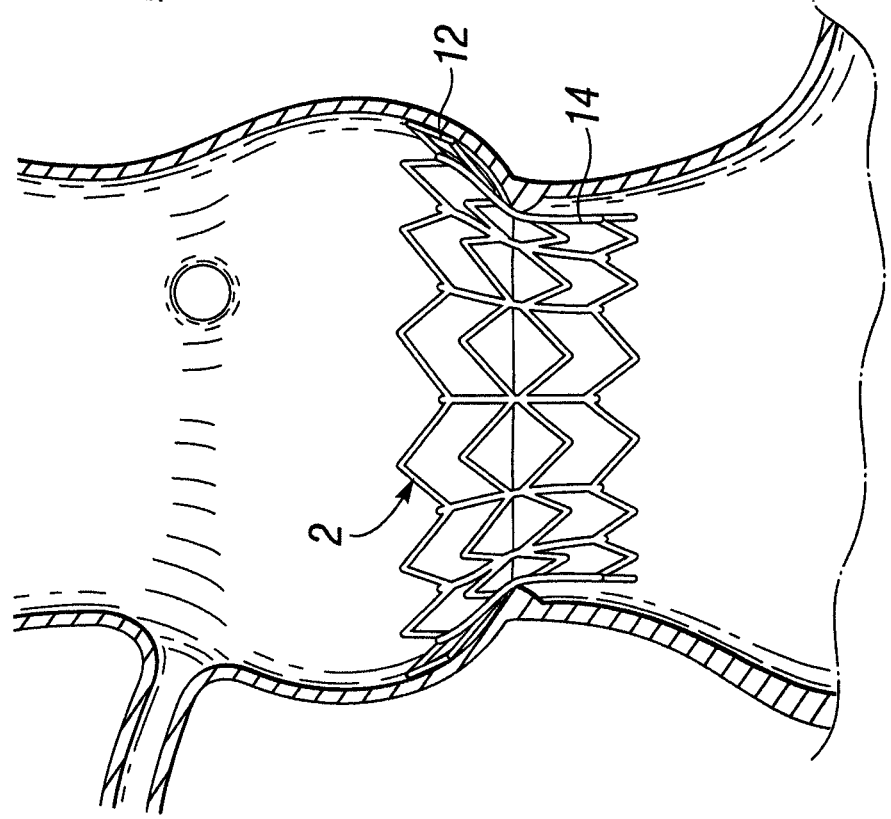

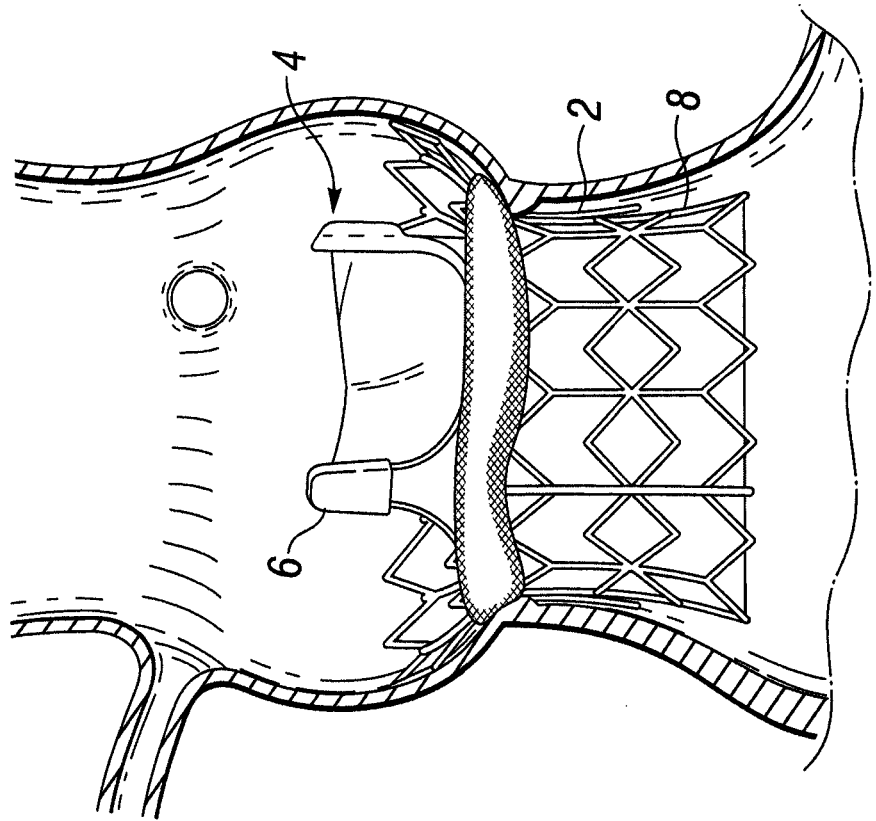
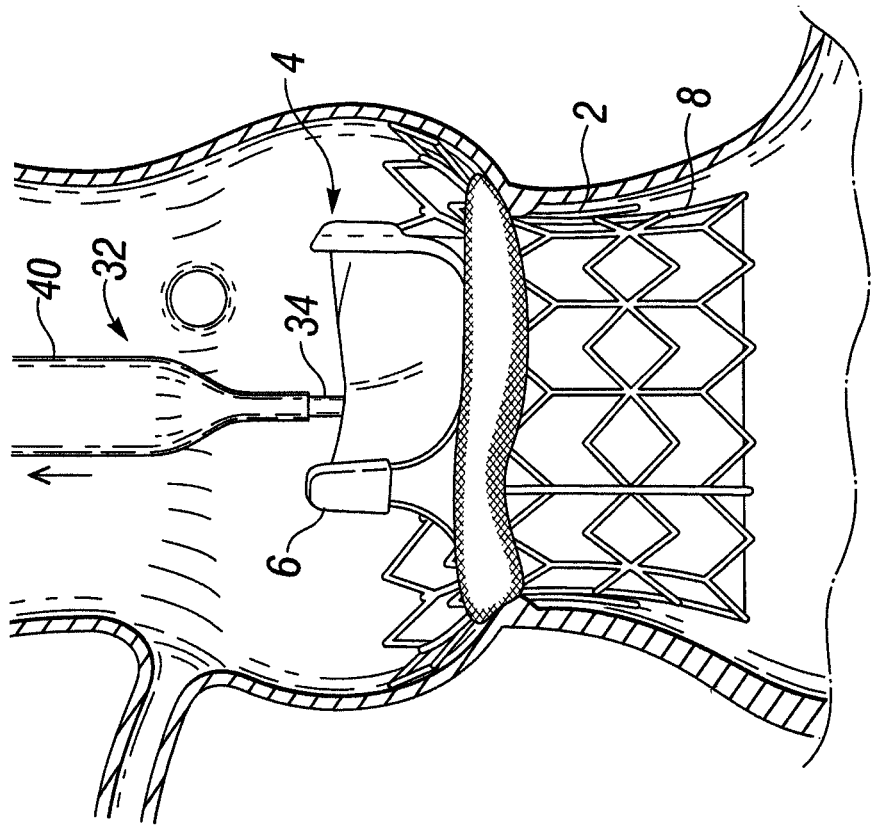

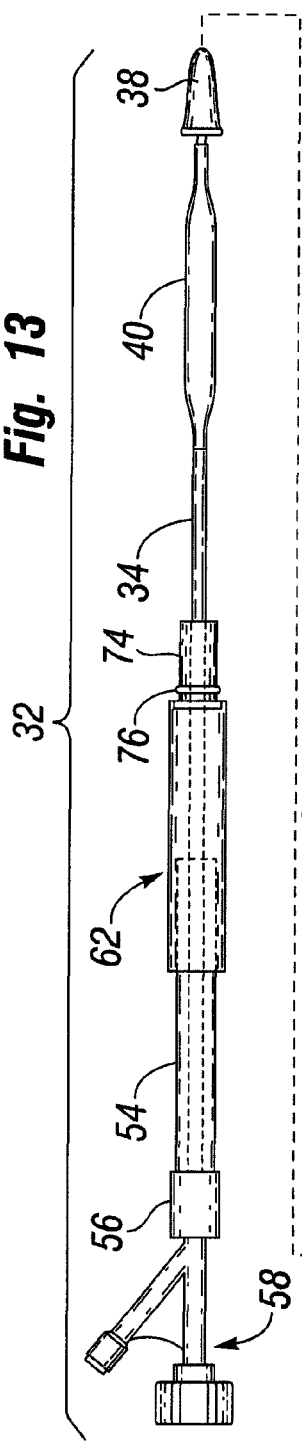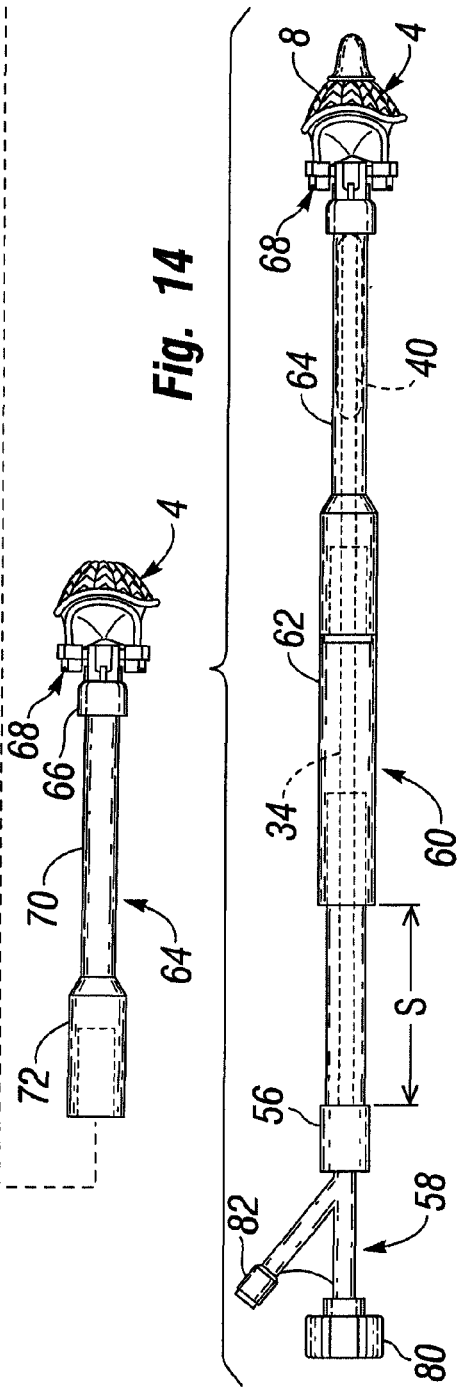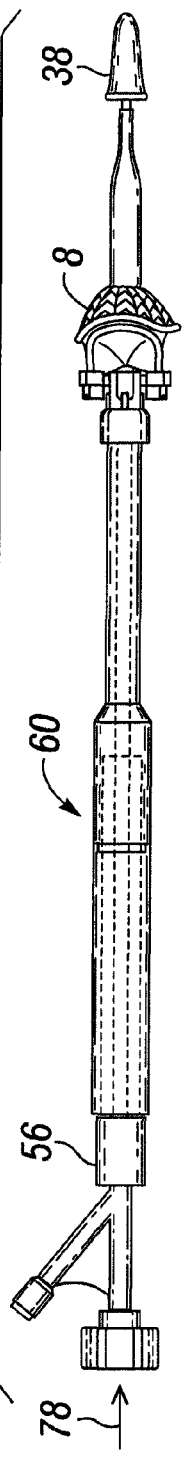

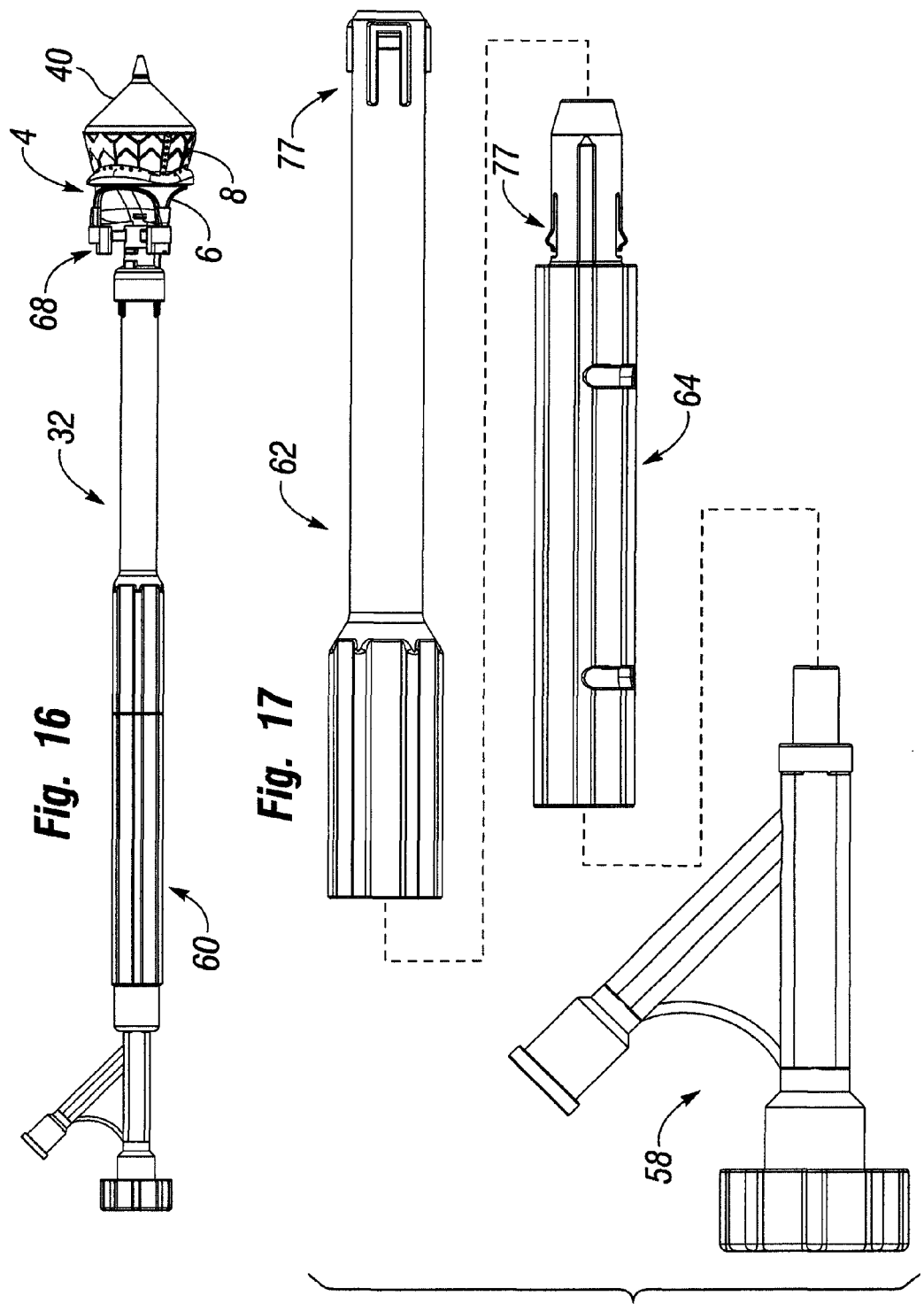

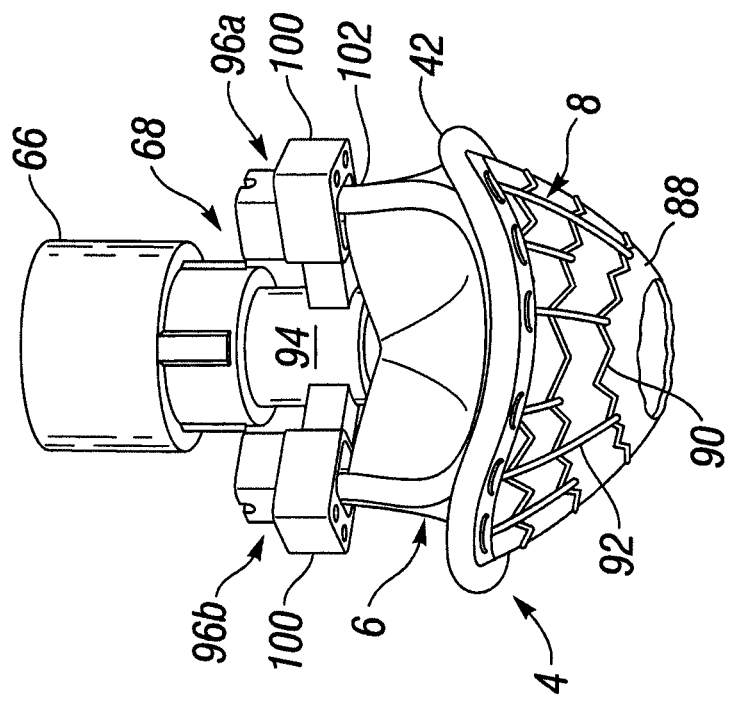
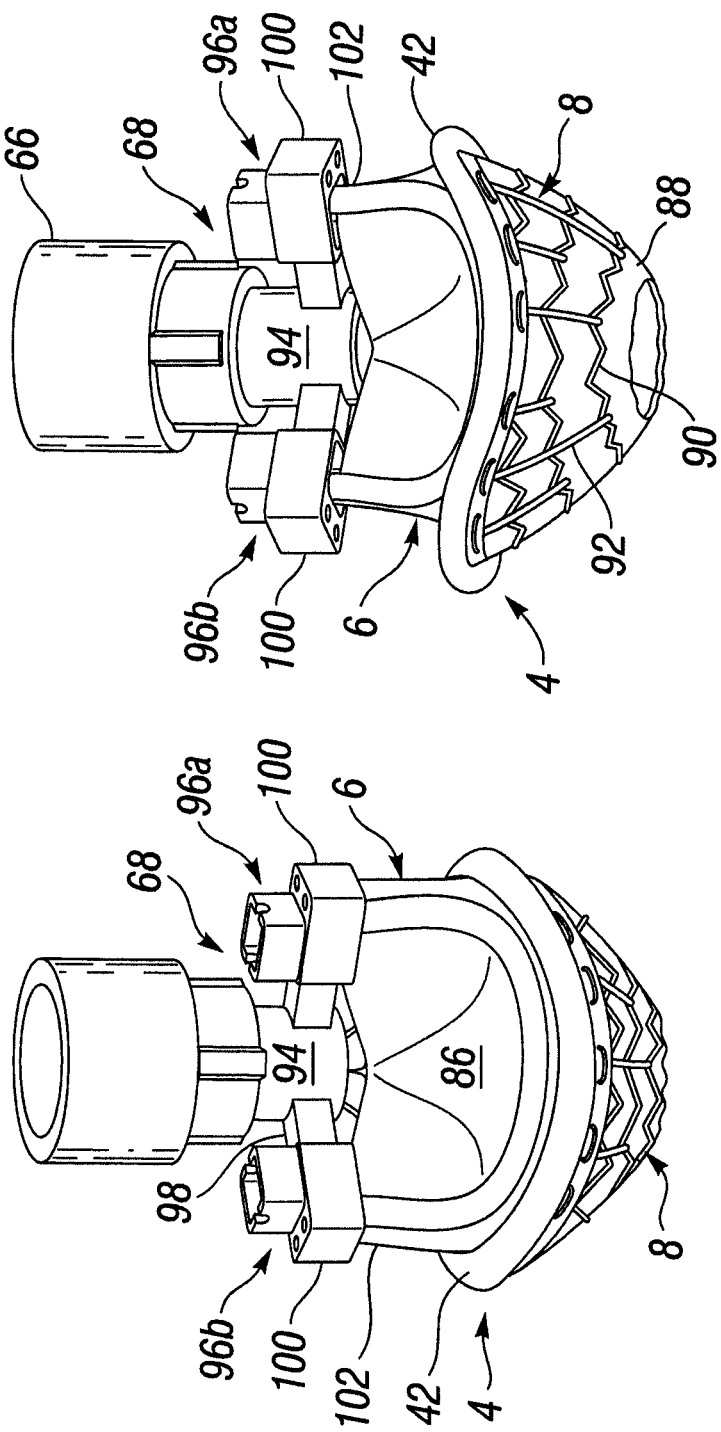

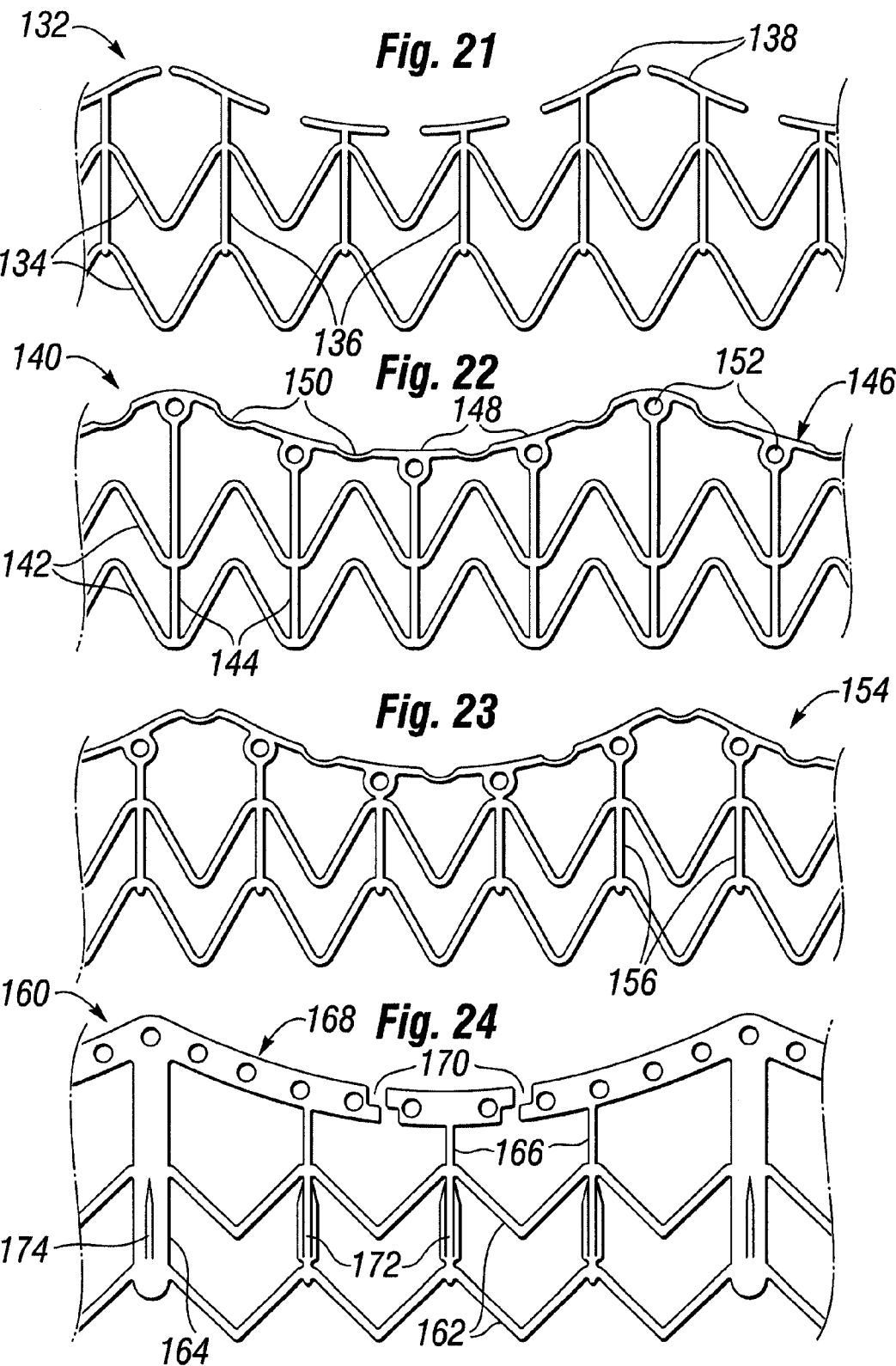

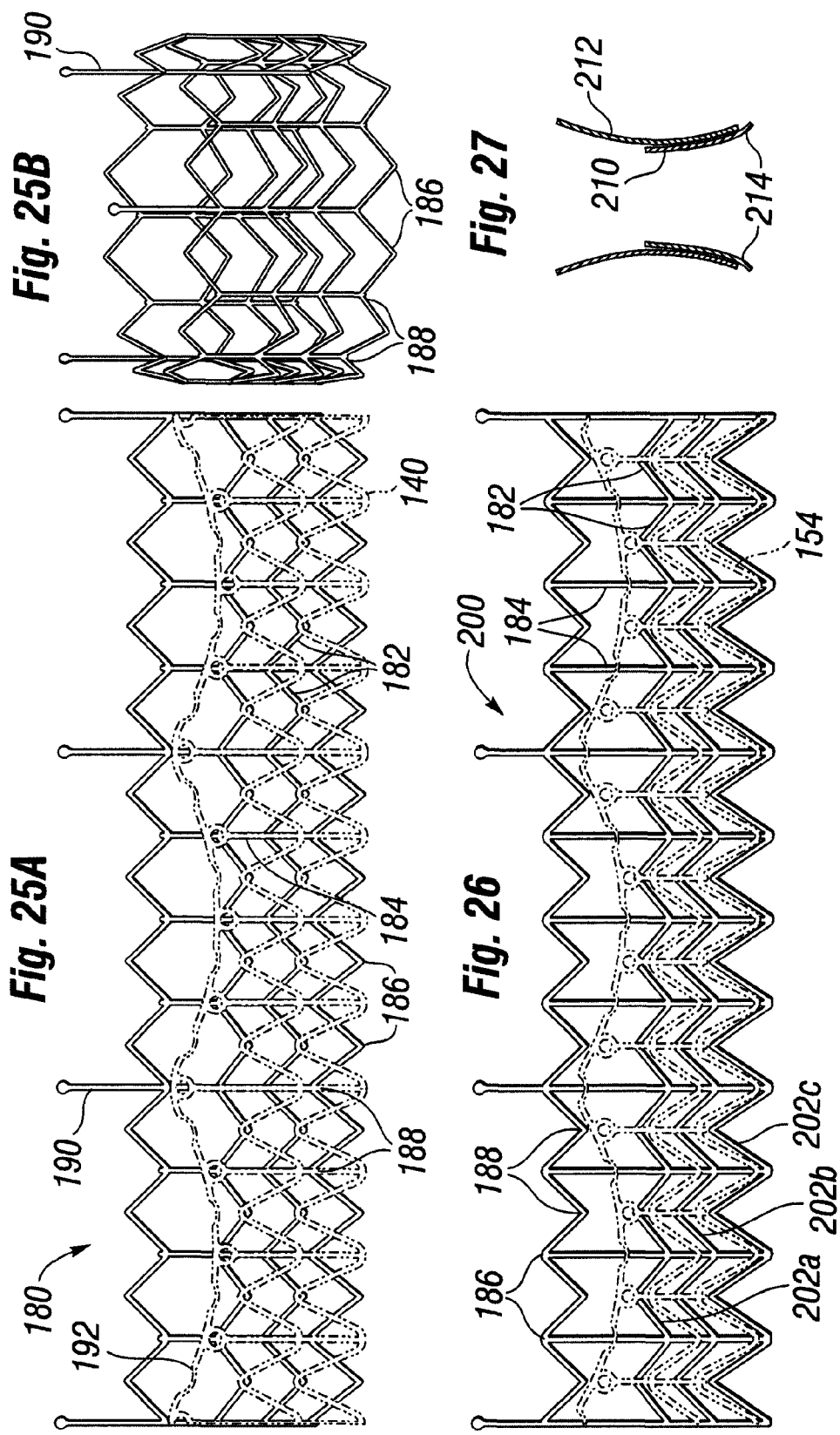

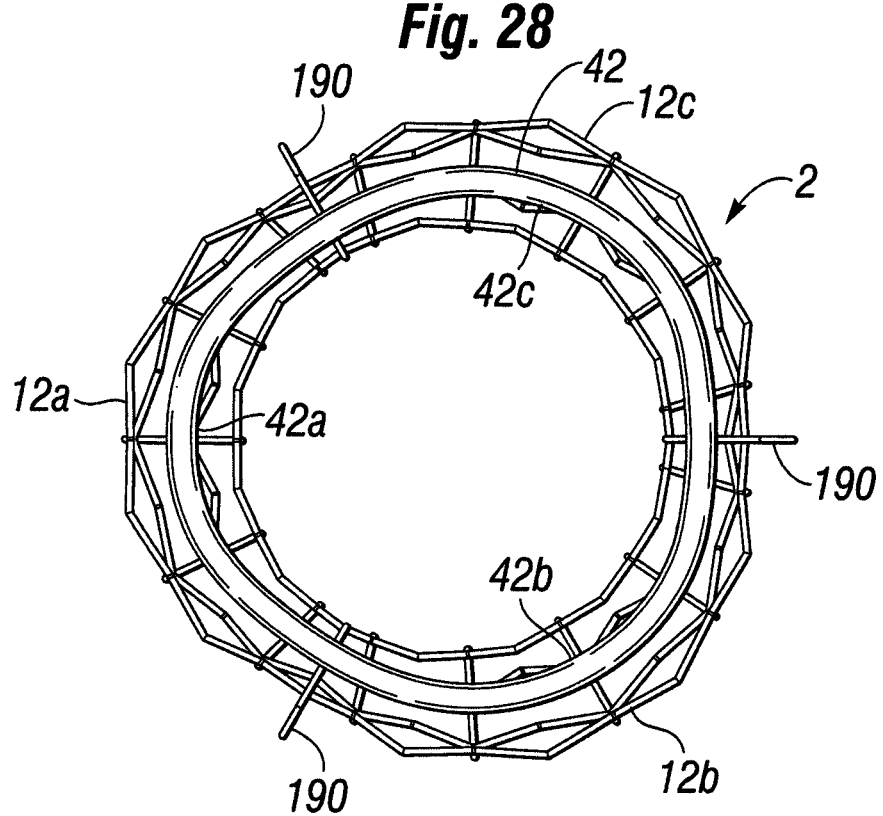
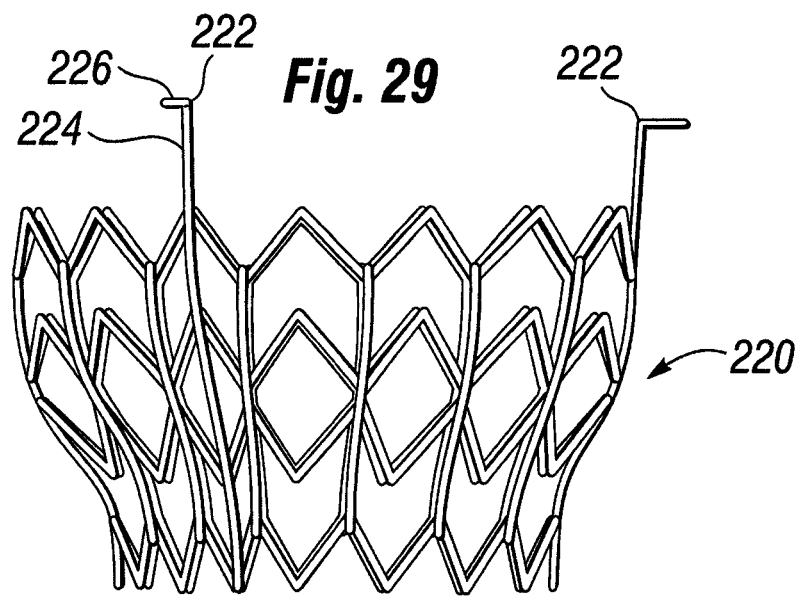

METHODS OF IMPLANTING A HEART VALVE AT AN AORTIC ANNULUS

RELATED APPLICATIONS

The present application is a division of U.S. application Ser. No. 12/716,961, filed Mar. 3, 2010, now U.S. Pat. No. 9,248,016, which claims the benefit under 35 U.S.C. § 119(e) to U.S. Application No. 61/165,455, filed Mar. 31, 2009, the entire disclosures of which are incorporated by reference in their entireties.

FIELD OF THE INVENTION

The present disclosure generally relates to method of implantation of a prosthetic valve at an aortic annulus.

BACKGROUND OF THE INVENTION

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 4 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,522 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure. The present invention addresses these needs and others.

SUMMARY OF THE INVENTION

According to one aspect of the present technology, a two-stage prosthetic heart valve system is provided wherein the tasks of implanting a tissue anchor first and then a valve member are distinct and certain advantages result. An exemplary two-stage prosthetic heart valve system has a first prosthesis or component in the form of an expandable base stent, or support frame, that is radially expanded to secure to surrounding tissue in the appropriate location using a balloon or other expansion technique. The two-stage heart valve system has a second prosthesis or component including a prosthetic valve that is delivered to and mounted within the base stent in a separate or sequential operation after the base stent has been anchored to the implantation site. The second prosthesis in certain embodiments comprises a hybrid valve component that has non-expandable and expandable portions. For example, the hybrid valve component can comprise a conventional, non-expandable surgical valve (i.e., a prosthetic valve that is sutured to a native valve annulus during open-heart surgery) that is modified to include an expandable coupling stent that can be expanded to engage the base stent, thereby anchoring the valve component to the base stent. By utilizing an expandable base stent in conjunction with an expandable coupling stent, the duration of the entire procedure is greatly reduced as compared with a conventional sewing procedure utilizing an array of sutures. The expandable base stent may simply be radially expanded outward into contact with the implantation site, and/or may be provided with additional anchoring means, such as barbs. The operation may be carried out using a conventional open-heart approach and cardiopulmonary bypass. In one advantageous feature, the time on bypass is greatly reduced due to the relative speed of implanting the expandable base stent and the valve component compared to the time required to implant a conventional surgical valve using sutures.

In certain embodiments, the base stent is plastically expandable and is expanded adjacent the implantation site using an expansion tool that expands the stent to a predetermined configuration. In its expanded configuration, at least a portion of the base stent has a generally cloverleaf or tri-lobular shape that mimics the shape of the sinuses at the aortic root. The tri-lobular shaped portion of the base stent closely conforms to the aortic root where the base stent is deployed to minimize paravalvular leaks between the base stent and the annulus of the native valve. The valve component can utilize a commercially available, off-the-shelf aortic surgical valve, which typically has a generally tri-lobular shaped sewing ring. The tri-lobular shaped portion of the base stent serves as a seating area for receiving the sewing ring of the prosthetic valve. Advantageously, the seating area of the base stent closely conforms to the shape of the sewing ring to minimize paravalvular leaks between the base stent and the prosthetic valve.

The base stent in its expanded configuration desirably has a flared outflow end portion that tapers down to a smaller diameter inflow end portion. The base stent can be positioned such that the inflow end portion extends through and engages the surrounding tissue of the aortic annulus. In this manner, the inflow end portion serves as a tissue anchor for anchoring the base stent in place within the native aortic valve. As noted above, additional anchoring means, such as barbs, can extend from the base stent to assist in anchoring the base stent in place. Desirably, the outflow end portion of the base stent is expanded to have a tri-lobular cross-sectional shape and is positioned in the Valsalva sinuses just above the aortic annulus. The outflow end of the base stent desirably has a diameter that is larger than the outer diameter of the valve component (typically defined by the sewing ring of the valve component) so that once the base stent is implanted, the valve component (including a prosthetic valve), can be advanced through the outflow end and anchored within the base stent. The sewing ring of the valve component desirably is seated against the tri-lobular shaped portion of the base stent at a location just above the aortic annulus, and a coupling stent of the valve component extends downwardly into the inflow end portion of the base stent. The coupling stent can then be expanded to engage the inner surface of the inflow end portion of the base stent, thereby anchoring the valve component to the base stent.

In a representative embodiment, a prosthetic heart valve system comprises a plastically-expandable base stent adapted to anchor against a heart valve annulus. The base stent is radially expandable from a compressed configuration to an expanded configuration, wherein at least a portion of the stent in the expanded configuration has a tri-lobular cross-sectional profile in a plane perpendicular to a longitudinal axis of the base stent.

In another representative embodiment, a prosthetic heart valve system comprises a prosthetic valve comprising a support frame and valve leaflets supported by the support frame. The system further includes a radially-expandable base stent adapted to anchor against a heart valve annulus, the base stent being radially expandable from a compressed configuration for delivery to the annulus to an expanded configuration for receiving the prosthetic valve. In its expanded configuration, the base stent has an outflow end having a first diameter and an inflow end having a second diameter smaller that the first diameter. The expanded base stent also comprises an outflow end portion that tapers down to an inflow end portion, with at least a portion of the outflow end portion having a tri-lobular shape, and the outflow end being sized to allow the prosthetic valve to be inserted into the base stent such that the support frame can be mounted within the outflow end portion.

In another representative embodiment, a prosthetic heart valve system comprises a delivery apparatus comprising an expansion device having an outer mounting surface. The system further includes a radially-expandable stent mounted in a radially compressed state on the mounting surface of the expansion device, the stent being adapted to anchor against a heart valve annulus. The expansion device is configured to expand radially outward from a first, compressed configuration to a second, expanded configuration to expand the stent to an expanded state, wherein the mounting surface is shaped to cause at least a portion of the stent to assume a tri-lobular cross-sectional profile when expanded.

In another representative embodiment, a method of implanting a prosthetic heart valve system is provided. The method comprises advancing a base stent to an implant position adjacent a heart valve annulus and radially expanding the base stent so as to anchor the base stent to the heart valve annulus, the expanded base stent having an outflow end portion and an inflow end portion, at least a portion of the outflow end portion having a tri-lobular cross-sectional profile. The method further includes providing a prosthetic valve having a non-expandable, non-collapsible ring and valve leaflets coupled to the ring, advancing the prosthetic valve into the outflow end portion of the base stent, and anchoring the prosthetic valve to the base stent.

The foregoing and other features and advantages of the invention will become more apparent from the following detailed description, which proceeds with reference to the accompanying figures.

BRIEF DESCRIPTION OF THE DRAWINGS

FIG. 7 is a perspective view of a delivery apparatus, according to one embodiment, that can be used to the deliver and implant a base stent in the aortic annulus.

FIGS. 10A and 10B are top plan views of the shape-forming members in the expanded and collapsed configurations, respectively, shown apart from the balloon for purposes of illustration.

FIGS. 11A and 11B are side views of the shape-forming members in the expanded and collapsed configurations, respectively, shown apart from the balloon for purposes of illustration.

FIGS. 12A-12H are sectional views through an isolated aortic annulus showing a portion of the adjacent left ventricle and aorta, and illustrating a number of steps in deployment of an exemplary prosthetic heart valve system.

FIG. 12A shows a deflated balloon catheter having a base stent thereon advanced into position at the aortic annulus.

FIG. 12B shows the balloon on the catheter inflated to expand and deploy the base stent against the aortic annulus.

FIG. 12C shows the deployed base stent in position within the aortic annulus.

FIG. 12D shows a valve component mounted on a balloon catheter of a delivery apparatus advancing into position within the base stent.

FIG. 12E shows the valve component in a desired implant position at the aortic annulus and within the base stent, with the balloon catheter advanced farther to displace a nose cone out of engagement with a coupling stent.

FIG. 12F shows the balloon on the catheter inflated to expand and deploy a valve component coupling stent against the base stent.

FIG. 12G shows the deflated balloon on the catheter along with the nose cone being removed from within the deployed valve component.

FIG. 12H shows the fully deployed, two-stage prosthetic heart valve system.

FIG. 13 is an exploded view of an exemplary system for introducing and implanting a valve component of a two-stage heart valve system.

FIG. 14 is an assembled view of the introducing system of FIG. 13 showing a nose cone extending over a distal end of a valve component coupling stent.

FIG. 15 is a view like FIG. 14 but with a balloon catheter displaced distally to disengage the nose cone from the coupling stent.

FIG. 16 is an assembled view of the introducing system similar to that shown in FIG. 14 and showing a balloon inflated to expand the valve component coupling stent.

FIG. 17 is an exploded elevational view of several components of the introducing system of FIG. 16, without the balloon catheter, valve component and holder.

FIGS. 18A and 18B are perspective views of an exemplary valve component assembled on a delivery holder.

FIGS. 21-24 are flat views of a still further alternative coupling stents.

FIGS. 25A-25B are flat and tubular views of an exemplary base stent with upper position markers.

FIG. 26 is a flat view of an alternative base stent with a coupling stent superimposed thereover.

FIG. 27 is a sectional view of a coupling stent within a base stent illustrating one method of interlocking.

FIG. 28 is a top plan view showing the sewing ring of a prosthetic valve mounted within a base stent.

FIG. 29 is a side view of an alternative base stent with position markers.

DETAILED DESCRIPTION OF THE PREFERRED EMBODIMENTS

Overview of Two-Stage Heart Valve System

Figure 1:
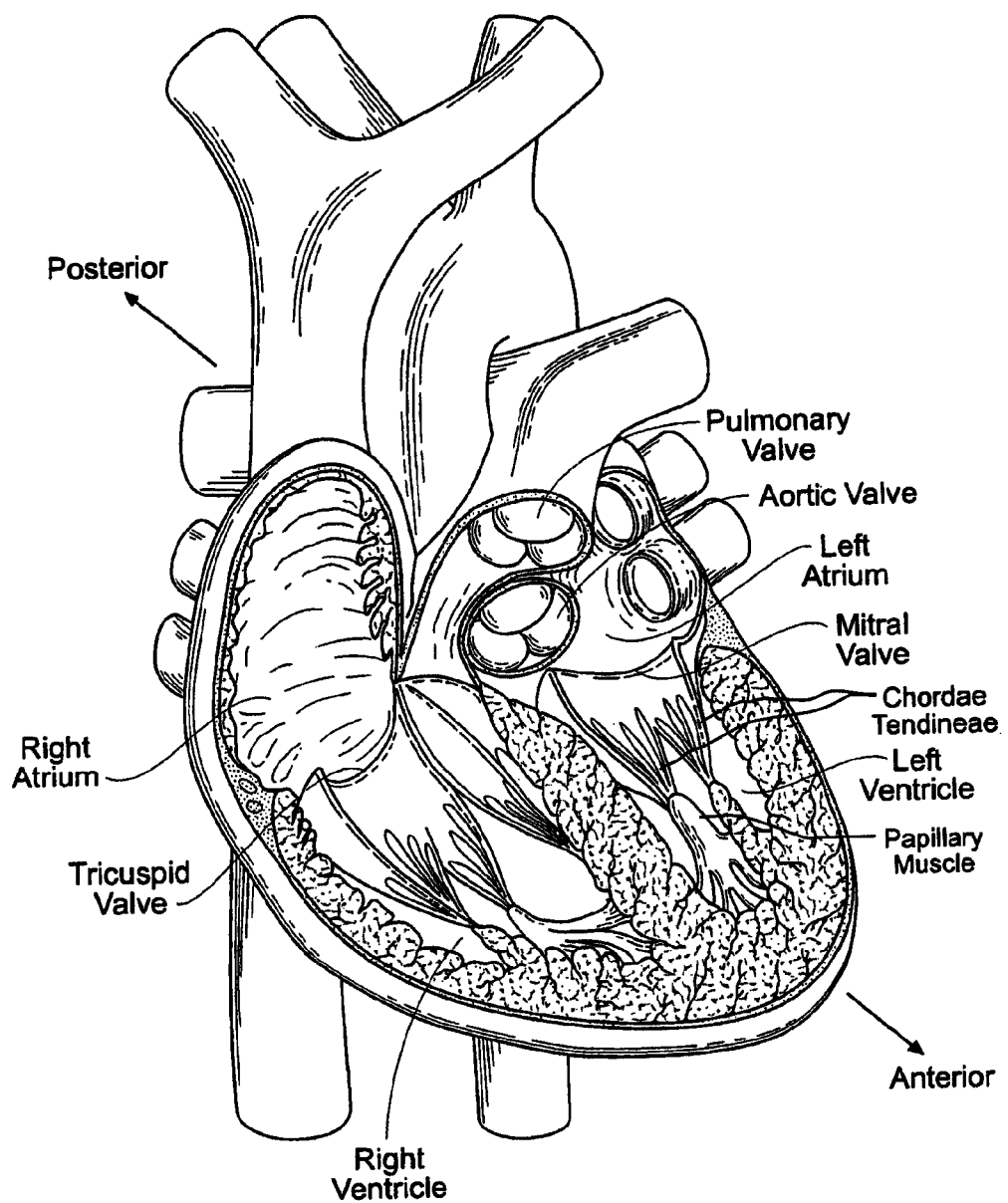
FIG. 1 is an anatomic anterior view of a human heart, with portions broken away and in section to view the interior heart chambers and adjacent structures.
Figure 2:
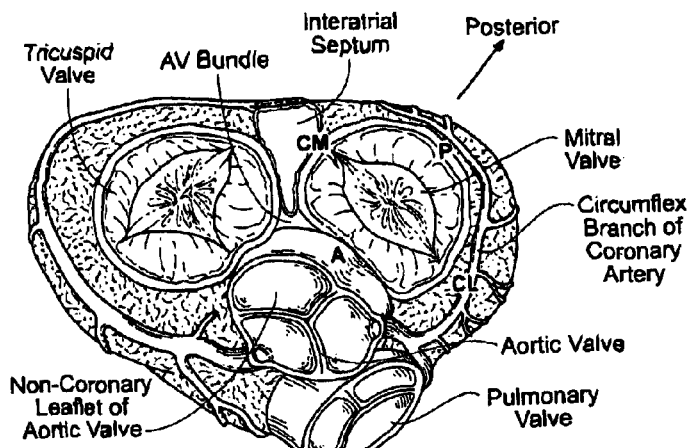
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
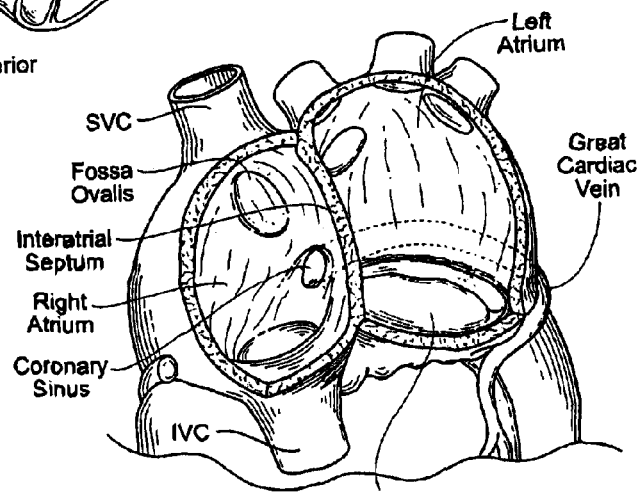
FIG. 4 is an anatomic anterior perspective view of the left and right atriums, with portions broken away and in section to show the interior of the heart chambers and associated structures, such as the fossa ovalis, coronary sinus, and the great cardiac vein.
Figure 3:
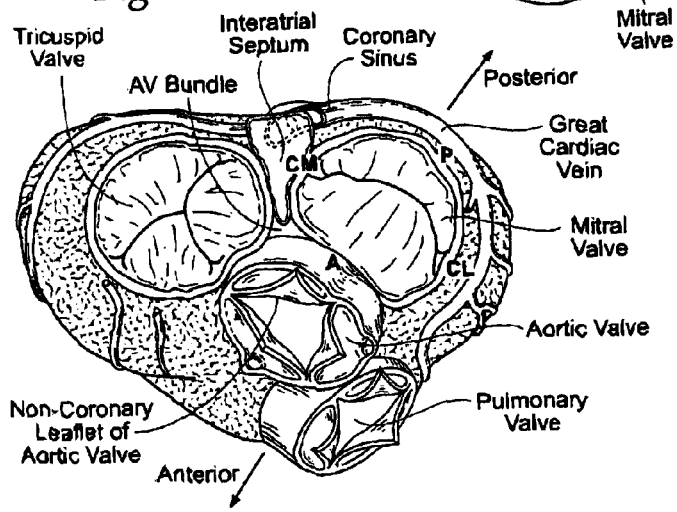
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.

Certain embodiments of the present technology attempt to overcome drawbacks associated with conventional, open-heart surgery, while also adopting some of the techniques of newer technologies which decrease the duration of the treatment procedure. The prosthetic heart valves of the present disclosure can be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the two-stage prosthetic heart valves described herein may also be configured for delivery using percutaneous approaches, and those minimally-invasive surgical approaches that require remote implantation of the valve using indirect visualization.

According to one aspect of the present technology, a two-stage prosthetic heart valve system is provided wherein the tasks of implanting a tissue anchor first and then a valve member are distinct and certain advantages result. An exemplary two-stage prosthetic heart valve has an expandable base stent, or support frame, secured to tissue in the appropriate location using a balloon or other expansion technique. A hybrid valve member that has non-expandable and expandable portions then couples to the base stent in a separate or sequential operation. By utilizing an expandable base stent, the duration of the initial anchoring operation is greatly reduced as compared with a conventional sewing procedure utilizing an array of sutures. The expandable base stent may simply be radially expanded outward into contact with the implantation site, and/or may be provided with additional anchoring means, such as barbs. The operation may be carried out using a conventional open-heart approach and cardiopulmonary bypass. In one advantageous feature, the time on bypass is greatly reduced due to the relative speed of implanting the expandable base stent compared to the time required to implant a conventional surgical valve using sutures.

For definitional purposes, the term "base stent," refers to a structural component of a heart valve prosthesis that is capable of attaching to tissue of a heart valve annulus. The base stents described herein are most typically tubular stents, or stents having varying shapes or diameters. A stent is normally formed of a biocompatible metal wire frame, such as stainless steel or Nitinol. Other base stents that could be used with valves of the present invention include rigid rings, spirally-wound tubes, and other such tubes that fit tightly within a valve annulus and define an orifice therethrough for the passage of blood, or within which a valve member is mounted. It is entirely conceivable, however, that the base stent could be separate clamps or hooks that do not define a continuous periphery. Although such devices sacrifice some dynamic stability, and speed and ease of deployment, these devices could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a compressed diameter to an expanded diameter. It should be understood that the term balloon-expanding stents encompasses plastically-expandable stents, whether or not a balloon is used to actually expand it. The material of the stent plastically deforms after application of a deformation force such as an inflating balloon or expanding mechanical fingers. Both alternatives will be described below. Consequently, the term "balloon-expandable stent" should be considered to refer to the material or type of the stent as opposed to the specific expansion means.

The term "valve member" refers to that component of a heart valve assembly that possesses the fluid occluding surfaces to block blood flow in one direction while permitting it in another. As mentioned above, various constructions of valve members are available, including those with flexible leaflets and those with rigid leaflets or a ball and cage arrangement. The leaflets may be bioprosthetic, synthetic, or metallic.

A primary focus of certain embodiments of the present technology is a two-stage prosthetic heart valve having a first stage in which a base stent secures to a valve annulus, and a subsequent second stage in which a valve member connects to the base stent. It should be noted that these stages can be done almost simultaneously, such as if the two components were mounted on the same delivery device, or can be done in two separate clinical steps, with the base stent deployed using a first delivery device, and then the valve member using another delivery device. It should also be noted that the term "two-stage" refers to the two primary steps of anchoring structure to the annulus and then connecting a valve member, which does not necessarily limit the valve to just two parts.

Another potential benefit of a two-stage prosthetic heart valve, including a base stent and a valve member, is that the valve member may be replaced after implantation without replacing the base stent. That is, an easily detachable means for coupling the valve member and base stent may be used that permits a new valve member to be implanted with relative ease. Various configurations for coupling the valve member and base stent are described herein.

It should be understood, therefore, that certain benefits of the invention are independent of whether the base stent is expandable or not. That is, various embodiments illustrate an expandable base stent coupled to a hybrid valve member that has non-expandable and expandable portions. However, the same coupling structure may be utilized for a non-expandable base stent and hybrid valve member. Therefore, the invention should be interpreted via the appended claims.

As a point of further definition, the term "expandable" is used herein to refer to a component of the heart valve capable of radially expanding from a first, compressed state for delivery to a second, expanded state. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

In the description that follows, the term "body channel" is used to define a conduit or vessel within the body (e.g., a blood vessel). Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present technology are particularly advantageous for one implantation site or the other. However, unless the combination is structurally impossible, or excluded by claim language, any of the heart valve embodiments described herein could be implanted in any body channel. Furthermore, in addition to heart valves, the technology disclosed herein can be used for implanting a prosthetic valve into many types of vascular and nonvascular body lumens (e.g., veins, arteries, esophagus, ducts of the biliary tree, intestine, urethra, fallopian tube, other endocrine or exocrine ducts, etc.).

FIGS. 12A-12H are sectional views through an isolated aortic annulus AA showing a portion of the adjacent left ventricle LV and ascending aorta with sinus cavities S. The two coronary sinuses CS are also shown. The series of views show snapshots of a number of steps in deployment of an exemplary prosthetic heart valve system, which comprises a two-component system. A first prosthesis, or component, is a base stent 2 that is deployed against the native leaflets or, if the leaflets are excised, against the debrided aortic annulus AA. A second prosthesis, or component, comprises a valve component 4 that fits within the base stent 2 and anchors thereto. The valve component 4 generally comprises a prosthetic valve 6 and a coupling stent 8, which are described in detail below. Although two-part valves are known in the art, this is believed to be the first that utilizes a stent within a stent in conjunction with a non-expandable valve.

The base stent 2 provides a base within and against a body lumen (e.g., a valve annulus). Although a stent is described for purposes of illustration, any member capable of anchoring within and against the body lumen and then coupling to the valve component may be used. In particular embodiments, the base stent 2 comprises a plastically-expandable cloth-covered stainless-steel tubular stent. One advantage of using a plastically-expandable stent is the ability to expand the native annulus to receive a larger valve size than would otherwise be possible with conventional surgery, which can decrease morbidity and mortality. Alternatively, embodiments of the present technology could also use a self-expanding base stent 2 which is then reinforced by the subsequently implanted valve component 4. Because the valve component 4 has a non-compressible part, the prosthetic valve 6, and desirably a plastically-expandable coupling stent 8, it effectively resists recoil of the self-expanded base stent 2. Although a self-expanding base stent can be used to enlarge the native annulus, a plastically-expandable stent generally undergoes much less recoil than a self-expanding stent after deployment. Hence, a plastically-expandable base stent is more effective in enlarging the native annulus than a self-expanding base stent.

Figure 6:
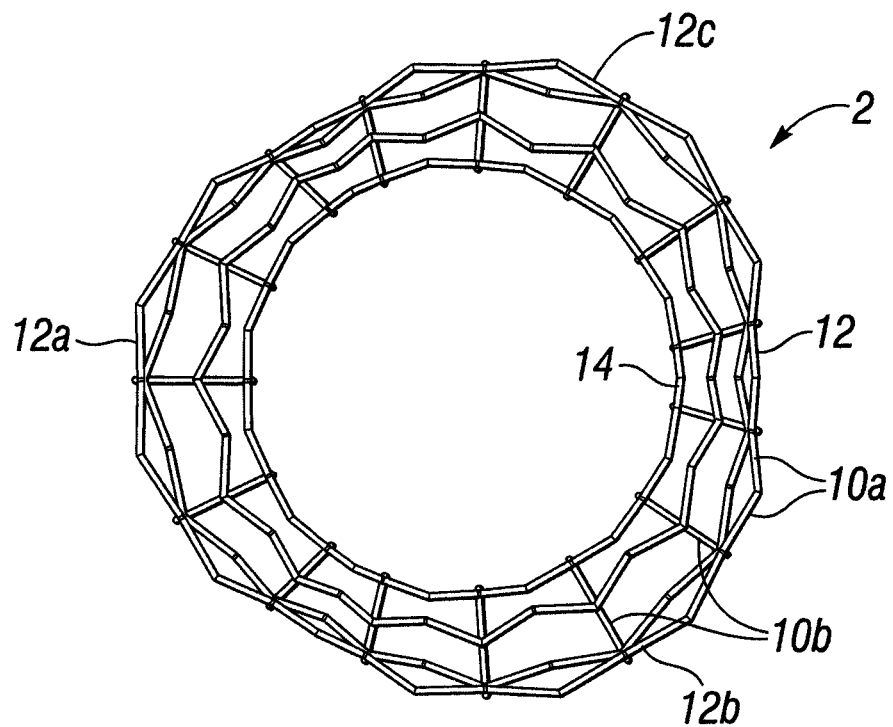
FIG. 6 is a top plan view of the base stent shown in FIG. 5.
Figure 5:
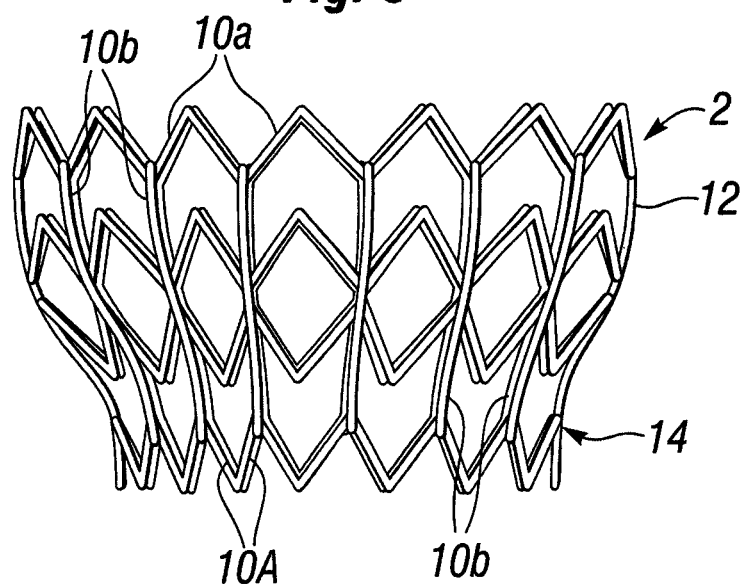
FIG. 5 is a side elevation view of a base stent, according to one embodiment, that can be used in a two-stage heart valve system.

FIG. 5 is a side elevation view of one embodiment of a base stent 2 of a two-stage heart valve and FIG. 6 is a top plan view of the base stent 2. The base stent 2 is configured to be radially expandable from a collapsed, or crimped, state (for delivery on a delivery device to the desired deployment site) to an expanded state shown in FIGS. 5 and 6. As shown, the base stent 2 can have an open-frame construction formed from a plurality of zig-zag shaped struts 10a interconnected by a plurality of angularly spaced, longitudinally extending struts 10b. The stent can have an outer covering (not shown) covering the struts (or portions thereof) to promote ingrowth and/or to reduce paravalvular leakage. For example, a suitable cover that can be used is a sleeve of fabric such as Dacron.

FIG. 7 shows a delivery device 16, according to one embodiment, that can be used to deliver and deploy the base stent 2. The delivery device 16 is configured to expand the base stent 2 to the expanded shape shown in FIGS. 5 and 6. As shown, the expanded base stent 2 has a flared or enlarged outflow end portion 12 and an inflow end portion 14 having a reduced diameter. Thus, the base stent 2 tapers from a first diameter at the outflow end portion 12 to a second, smaller diameter at the inflow end portion 14. As best shown in FIG. 6, the outflow end portion 12 of the expanded stent desirably has a generally cloverleaf or tri-lobular shape having three sinus-shaped regions 12a, 12b, 12c so as to mimic the tri-lobular shape of the aortic root, the significance of which is discussed below.

It should be noted here that the base stents described herein can be a variety of designs, including having the diamond/chevron-shaped openings shown or other configurations. The material depends on the mode of delivery (i.e., balloon- or self-expanding), and the stent can be bare strut material or covered to promote ingrowth and/or to reduce paravalvular leakage.

One primary advantage of the prosthetic heart valve system is the speed of deployment. Therefore, the base stent 2 may take a number of different configurations but desirably does not require the time-consuming process of suturing it to the annulus. For instance, another possible configuration for the base stent 2 is one that is not fully expandable like the tubular stent as shown. That is, the base stent 2 may have a non-expandable ring-shaped orifice from which an expandable skirt stent and/or series of anchoring barbs deploy.

As noted above, the valve component 4 comprises a prosthetic valve 6 and a coupling stent 8 attached to and projecting from a distal end thereof. In its radially constricted or undeployed state, the coupling stent 8 assumes a conical inward taper in the distal direction (FIG. 12D). When used for aortic valve replacement, the prosthetic valve 6 desirably has three flexible leaflets which provide the fluid occluding surfaces to replace the function of the native valve leaflets. In particular embodiments, the valve leaflets may be taken from another human heart (cadaver), a cow (bovine), a pig (porcine valve) or a horse (equine). In other embodiments, the valve member may comprise mechanical components rather than biological tissue. The three leaflets can be supported by three commissural posts. A ring is provided along the base portion of the valve member.

In the illustrated embodiment, the prosthetic valve 6 has a non-expandable, non-collapsible support frame in the form of a sewing ring and flexible leaflets supported by the sewing ring (although the valve 6 need not be sutured or sewn to the base stent or to surrounding tissue). When the valve component is mounted within the base stent by expanding the coupling stent, the sewing ring seats against an inner surface of the base stent. The prosthetic valve can take various forms. For example, the prosthetic valve need not have a conventional sewing ring. Instead, the prosthetic valve can have a non-expandable, non-collapsible support frame, such as a non-expandable, non-collapsible stent, that mounts or supports leaflets or other mechanical components that form the occluding surfaces of the valve.

In one specific implementation, the prosthetic valve 6 partly comprises a commercially available, non-expandable prosthetic heart valve, such as the Carpentier-Edwards PERIMOUNT Magna® Aortic Heart Valve available from Edwards Lifesciences of Irvine, Calif. In this sense, a "commercially available" prosthetic heart valve is an off-the-shelf (i.e., suitable for stand-alone sale and use) prosthetic heart valve defining therein a non-expandable, non-collapsible orifice and having a sewing ring capable of being implanted using sutures through the sewing ring in an open-heart, surgical procedure. The particular approach into the heart used may differ, but in surgical procedures the heart is stopped and opened, in contrast to beating heart procedures where the heart remains functional. To reiterate, the terms "non-expandable" and "non-collapsible" should not be interpreted to mean completely rigid and dimensionally stable, merely that the valve is not expandable/collapsible like some proposed minimally-invasively or percutaneously-delivered valves.

Delivery Apparatus for Base Stent

FIG. 7 shows an embodiment of an apparatus 16 for delivering and expanding an expandable prosthetic device, such as the base stent 2, to conform to a non-circular anatomical shape of an orifice or conduit of the body. The delivery apparatus 16 in the illustrated embodiment includes a handle 18, a main, or outer, shaft 20a, an inner shaft 20b extending co-axially through the main shaft 20a, and an expansion device 21 (also referred to as an expander) mounted at the distal end of the inner shaft 20b. In the illustrated embodiment, the expansion device 21 comprises an inflatable balloon 22 mounted to the distal end of the inner shaft 20b. The balloon 22 has a plurality of longitudinally extending shape-forming members 24 (six, in this embodiment) that are spaced around the outer surface of the balloon 22 at angularly-spaced positions and form a part of the external structure of the balloon 22. The balloon 22 is shown in an inflated state in FIG. 7. Desirably, the inner shaft 20b comprises a lumen that extends from the proximal end of the handle 18 to the proximal end of the balloon 22. The lumen of the inner shaft 20b is in fluid communication with the balloon 22. An inflating device (not shown) can be connected to the proximal end of the shaft 20b, and a fluid that is capable of inflating the balloon 22 can be transferred from the inflating device through the lumen to balloon 22. Balloon inflating devices are well known and any conventional inflation means can serve to inflate the balloon 22 in order to expand the prosthetic device.

A prosthetic device (expandable member), such as the base stent 2, can be mounted on the shape-forming members 24. The expansion of the balloon 22 causes the shape-forming members 24 to move radially outward away from each other, which in turn expand the base stent 2 to conform to the external shape of the shape-forming members 24. The base stent 2 in the illustrated embodiment is adapted to be implanted within the native aortic valve and serves as a support structure for supporting a prosthetic valve deployed within the base stent 2.

Figure 8:
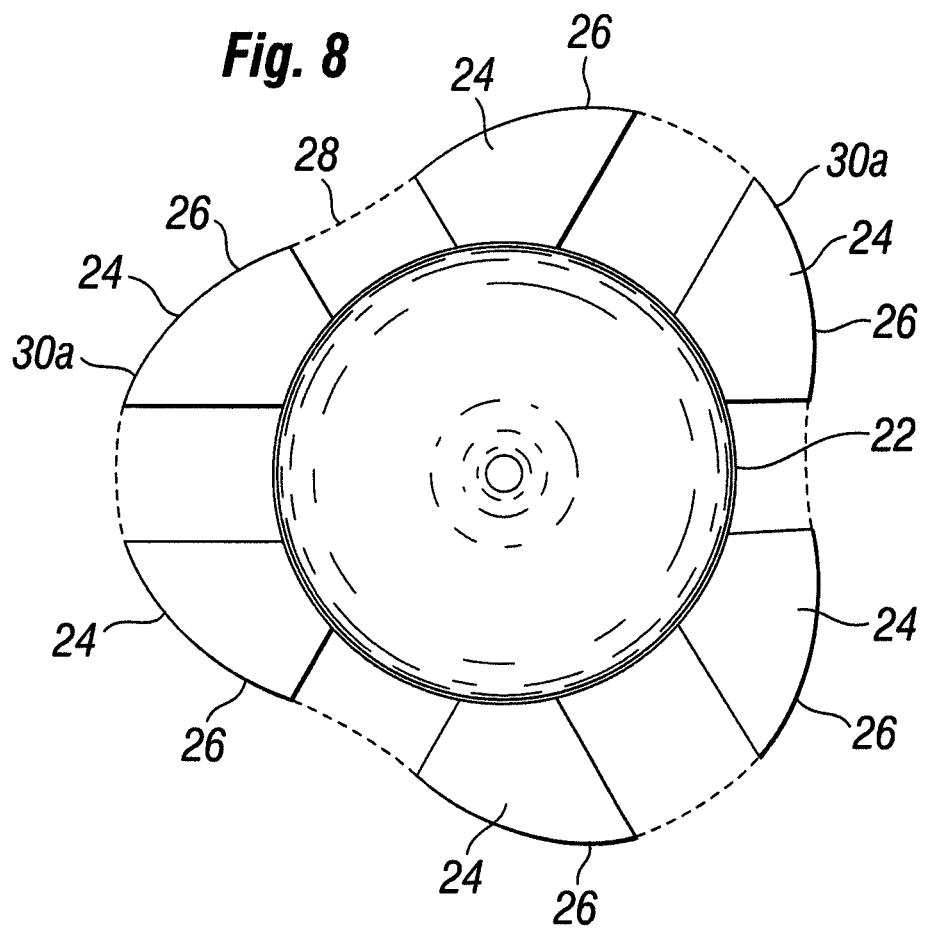
FIG. 8 is an end view of the delivery apparatus of FIG. 7 showing its balloon and shape-forming members in an expanded configuration.
Figure 9:
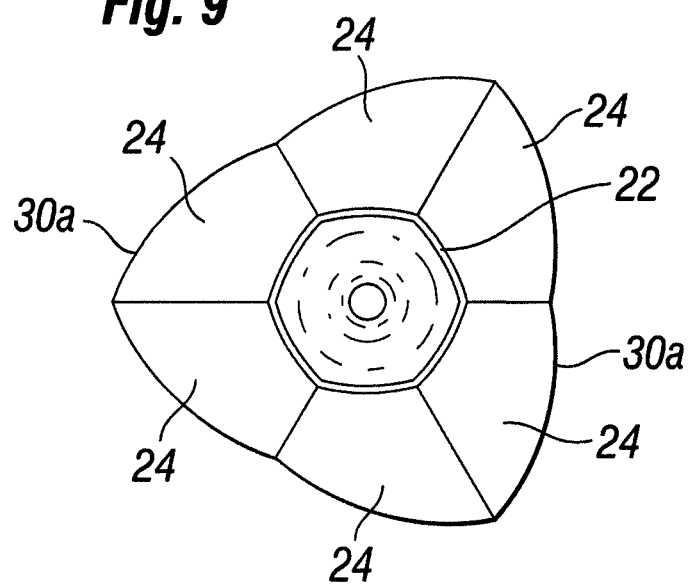
FIG. 9 is an end view of the delivery apparatus of FIG. 7 showing its balloon and shape-forming members in a radially collapsed, or compressed, configuration.

The shape-forming members 24 desirably have a cross-section that generally conforms to a non-cylindrical anatomical orifice or conduit in which the frame member is to be positioned and expanded. For example, the shape-forming members 24 shown in FIGS. 7-9 are configured to expand the base stent to conform to the anatomy of the annulus of an aortic valve. The collective cross-section of the shape-forming members 24 perpendicular to a main, or longitudinal, axis of the delivery apparatus 16 and the balloon is non-cylindrical. The main axis of a delivery apparatus or balloon is defined, for the purposes of this application, as the axis about which the expansion occurs. In this case, since the expansion is a result of the balloon 22 being inflated to a larger size, the main axis is the central axis of the balloon 22.

In the illustrated example, the shape of the shape-forming members 24 is configured so that when the balloon 22 is expanded, the outer surfaces of the shape-forming members 24 generally conform to the shape as the aortic root 22 at that location. Since the shape-forming members 24 are configured to conform to an anatomical geometry of an orifice or conduit, the base stent 2, when expanded by contact with shape-forming members 6 during expansion of balloon member 32, also generally conforms to the desired anatomical geometry (e.g., the aortic root).

It should be understood that for each embodiment discussed herein, the expansion device can be configured to expand a prosthetic device to generally conform to the non-circular shape of an anatomical orifice or conduit. Alternatively, for each embodiment discussed herein, the expansion device can be configured to expand a prosthetic device to generally conform to a non-circular shape of a second prosthetic device, which may or may not generally conform to a non-circular shape of the anatomical orifice or conduit in which the second prosthetic device is intended to be implanted.

FIG. 8 is a top end view of the shape-forming members 24 attached to the balloon 22 in an expanded configuration. The shape-forming member 24 can have external surfaces 26 that collectively form an outer perimeter of the shape-forming members 24. Although the collective external surfaces of the shape-forming members are discontinuous, an outer envelope curve 28 is defined by the collective external surfaces 26 and the imaginary lines connecting adjacent surfaces 26 (the dashed lines in FIG. 8). When the balloon 22 is expanded, the envelope curve 28 generally conforms to the curvature of the aortic root at the valve annulus. The shape-forming members 24 are desirably formed of a material that is rigid enough to impart the desired shape to the base stent 2 during expansion.

By placing the shape-forming members 24 at spaced locations around the balloon 22, the structure can be collapsed to a smaller diameter for delivery to the implantation site. For example, as shown in FIG. 9, the shape-forming members 24 can collapse so that the external surfaces 26 of the shape-forming members 24 collectively form a shape that has a smaller outer perimeter. The ability of shape-forming members 24 to collapse to a smaller profile permits the distal end of expander 16 to enter and exit an orifice or conduit more easily. In addition, each shape-forming member 24 desirably is sized so that it abuts adjacent shape-forming members 24 when the shape-forming members 24 are in a collapsed (non-expanded) configuration. For example, as shown in FIG. 9, each shape-forming member 24 is configured to contact adjacent shape-forming members 24 on two sides, in order to achieve a smaller profile when in the collapsed configuration. Desirably, in the collapsed configuration, the shape-forming members form a closed-ring shape, as shown in FIG. 9. When the balloon 22 is inflated, the shape-forming members 24 move radially outward to the expanded configuration shown in FIG. 8.

The shape-forming members 24 can have a variety of shapes and geometries, and can be formed in a variety of ways. In one approach, for example, the shape-forming members 24 can be formed by constructing a plurality of shape-forming members to conform to a model, such as a computer-aided design (CAD) model, of the conduit or orifice into which the base stent or other expandable member is to be positioned. In creating shape-forming members, a CAD model of the non-cylindrical orifice or conduit can be constructed (such as a model of the aortic root) and the relevant portion of the CAD model can be selected and sectioned. Certain sections can be selected and retained to maintain the general outer shape of the modeled conduit or orifice, and the remaining sections can be discarded. In this manner, separate and distinct pie-shaped pieces or sections of the shape-forming members can have discontinuous (spaced-apart) external surfaces that collectively define an envelope curve that approximates the shape of the anatomical orifice or conduit when the balloon member is expanded, while permitting the shape-forming members to achieve a smaller diameter (or profile) when the balloon member is deflated.

For example, FIGS. 10A and 10B show a plurality of shape-forming members 24 in an expanded configuration (without the balloon for purposes of illustration). The outer envelope 28 of the expanded configuration in plan view substantially forms the shape of the aortic valve annulus. Again, the shape-forming members have external surfaces that collectively form an outer envelope having a non-cylindrical shape perpendicular to a main axis of the expansion device. The shape-forming members 24 are desirably shaped to mate with the valve annulus, and tissue above the valve annulus in the aorta. Accordingly, in addition to having a shape that is non-cylindrical (when viewed from above, such as in FIG. 10A), the cross-sectional profile of the shape-forming members can vary along their length.

For example, each shape-forming member 24 in the illustrated embodiment includes a flared upper end portion 30a that tapers down to an intermediate portion 30b, and a lower end portion 30c that is slightly greater in width than the intermediate portion 30b. An expanded diameter $D_1$ defined by the flared upper portions 30a of the shape-forming members 24 (i.e., the portions that extend into the aorta) can be about 32 mm (or 1.260 inches), and an expanded diameter $D_2$ defined by the lower portions 30c of the shape-forming members 24 (i.e., the portion that extends into the left ventricle) can be about 23 mm (or 0.906 inches). In this manner, the base stent 2 can be expanded to form an enlarged upper portion that tapers to a smaller diameter lower portion to better conform to the aortic annulus and the aortic root immediately adjacent the annulus. As used herein, the term "diameter" is used to refer to the diameter of a circular cross-section and more generally to refer to the largest dimension of a non-circular cross-section measured between opposing points on the periphery of the non-circular cross-section. For example, the diameter of the shape-forming members at any location along the length of the expansion device is the largest dimension measured between opposing points on the outer envelope curve 28 formed by the collective surfaces of the shape-forming members at that location.

As noted above, because there are gaps or discontinuities between the shape-forming members 24 when they are in their expanded configuration, the shape-forming members 24 can have a smaller profile (or diameter) when the balloon is deflated. FIGS. 10B and 11B show a top plan view and side view, respectively, of the shape-forming members 24 in a non-expanded (collapsed) configuration. In this configuration, a non-expanded diameter $D_3$ defined by the upper portions 30a of the shape-forming members 24 (i.e., the portions that extend into the aorta) can be about 19 mm (or 0.74803 inches), and an non-expanded diameter $D_4$ defined by the lower portions 30c of the shape-forming members 24 (i.e., the portions that extend into the left ventricle) can be about 11.212 mm (or 0.12118 inches). Accordingly, the non-expanded configuration of shape-forming members 24 can be smaller than the expanded configuration of shape-forming members 24.

As noted above, the upper portions 30a of the shape forming members 24 are preferably non-circular. In one application, the upper portions 30a can be generally trilobular in cross section (perpendicular to a main axis of the expansion device) to generally conform to the shape of the aortic valve annulus. The lower portions 30c can be non-circular as well; however, it can be desirable to form the lower portions 30d so that they are generally circular, as shown in FIGS. 11A and 11B. In addition, the intermediate portion 30b of each shape-forming member can have a diameter that is smaller than the diameters of the upper portion 30a and the lower portion 30c.

As best shown in FIGS. 11A and 11B, the transition between the lower portion 30c and the intermediate portion 30b of each shape-forming member can include a lip portion 30d. The lip portions 30d can be used to assist in holding a prosthetic device (e.g., the base stent 2) in place on the expansion device 16 during delivery to the implantation site. For example, as shown in FIG. 12A, the base stent 2 can be mounted on the shape-forming members 24 such that the lower end 14 of the base stent abuts the lip portions 30d, thereby restricting movement of the base stent 2 in the distal direction during positioning and expansion of the base stent The number of shape-forming members 24 can vary. In the embodiments discussed above, there are six shape-forming members; however, there can be more or less than six members. In addition, the size of the shape-forming members can vary and the arc length of the shape-forming members can be made larger or smaller to reduce or increase, respectively, the number of shape-forming members that are used. In addition, the spaces or gaps between the shape-forming members can be increased or decreased depending on the particular requirements of the desired application.

The shape-forming members 24 can be adhered to the balloon 22 (or other expansion device) using adhesives and/or mechanical fasteners. In lieu of or in addition to using an adhesive and/or fastener to attach the shape-forming members to the balloon, it may be desirable to apply a sleeve member that forms a layer (or overcoat) of material over at least a portion of the external surfaces 26 of the shape-forming members and the balloon. The layer can be formed of a variety of materials, including, for example, silicone or other similar materials. If desirable, the sleeve can be formed by dip coating the balloon and shape-forming members 24 in a liquefied material, such as liquefied silicone or other similar materials. The overcoat layer can help the shape-forming members adhere to the balloon member, as well as serve as a protective material by reducing or eliminating any hard edges or points on the shape-forming members.

Other techniques and mechanisms can be used to deploy the base stent 2. For example, the delivery apparatus 16 can be configured to expand the shape-forming members 24 without the use of the balloon 22. In one implementation, the shape-forming members 24 are connected at their proximal ends to an outer shaft and an axially extending plunger mechanism extends through the outer shaft. The plunger mechanism can be pushed through the shape-forming members to cause them to move radially outward from each other from a first, collapsed state to a second, expanded state for expanding the base stent. In another implementation, the shape-forming members 24 are operatively connected to a handle mechanism through a series of linkages such that the shape-forming members are caused to move from a collapsed state to an expanded state via operation of the handle mechanism. Further details of alternative delivery apparatuses that can be used to expand the base stent to an expanded configuration having a tri-lobular shape that mimics the shape of the aortic root are disclosed in co-pending U.S. Application No. 61/117,902, filed Nov. 25, 2008, which is incorporated herein by reference.

Implantation of Two-Stage Heart Valve

Figure 12F:
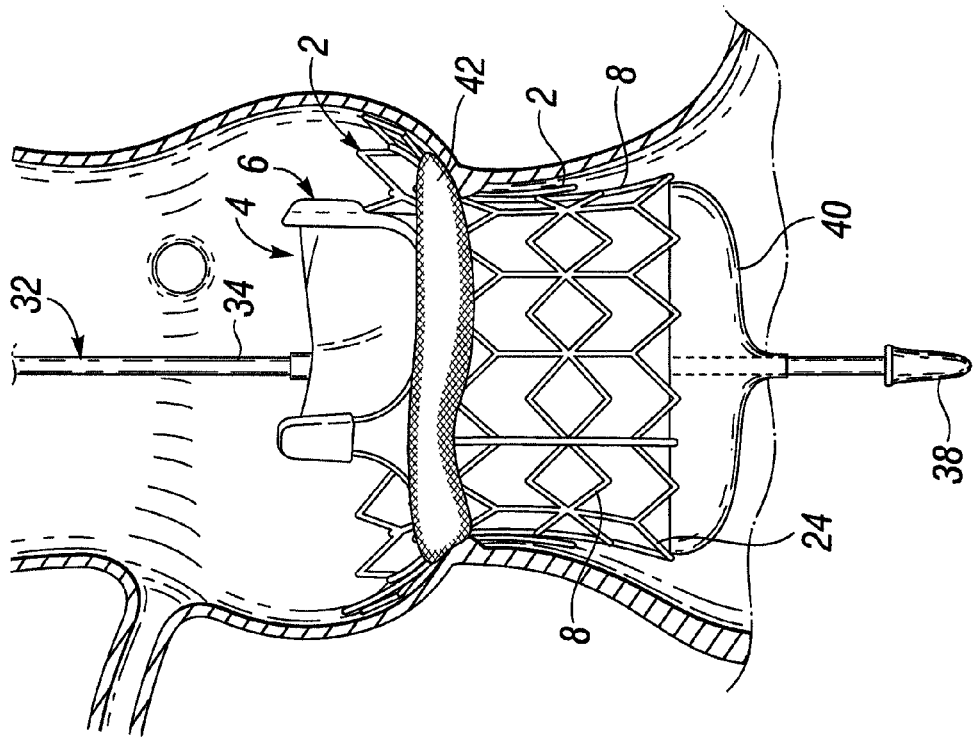

Referring again to FIGS. 12A-12H, one specific approach for implanting the base stent 2 and the valve component 4 will now be described. FIG. 12A shows the delivery device 16 with the balloon 22 in a deflated state near a distal end and the base stent 2 crimped thereover. The stent 2 is shown in a radially constricted, undeployed configuration. The delivery device 16 has been advanced to position the base stent 2 so that it is approximately axially centered at the aortic annulus AA. The surgeon can access the heart by any known surgical techniques. For example, access to the aortic valve can be achieved by an upper mini-sternotomy whereby incisions are made in the chest and the ascending aorta through which the base stent and the valve component are inserted on respective delivery apparatuses. Alternatively, as discussed in more detail below, the heart can be accessed percutaneously if so desired.

FIG. 12B shows the balloon 22 inflated to expand and deploy the base stent 2 against the aortic annulus AA, and FIG. 12C shows the deployed base stent in position after deflation of the balloon 22 and removal of the delivery device 16. As noted above, the stent 2 provides a base within and against a body lumen (e.g., a valve annulus) for mounting the valve component 4. With continued reference to FIG. 12B, the stent 2 has a diameter sized to be deployed at the location of the native valve (e.g., along the aortic annulus). A portion of the stent 2 may expand outwardly into the respective cavity adjacent the native valve. For example, in the aortic valve replacement shown in FIGS. 12A-12H, the upper (outflow) end portion 12 may expand into the area of the sinus cavities (the Valsalva sinuses) just downstream from the aortic annulus. Of course, care should be taken to orient the stent 2 so as not to block the coronary openings. The inflow end portion 14 of the stent can be positioned to extend into the left ventricle as shown. The outflow end portion 12 is expanded to a diameter large enough to allow the valve component 4 to be advanced into the base stent via the outflow end portion.

The base stent 2 can have visual position indicators, or markers, to assist the surgeon in positioning the base stent rotational and axially relative to the annulus AA. In one implementation, the stent 2 can have three position indicators in the form of three, equally spaced axially extending projections 190 (FIG. 28) that facilitate proper positioning of the stent by aligning the projections 190 with the native commissures of the native valve. The position markers are further discussed below.

The stent body is preferably configured with sufficient radial strength for pushing aside the native leaflets and holding the native leaflets open in a dilated condition. The native leaflets provide a stable base for holding the stent, thereby helping to securely anchor the stent in the body. In certain procedures, it may be desirable to excise the native leaflets before implanting the stent 2, in which case the remaining tissue of the native valve can serve as a suitable base for holding the stent in place. To further secure the stent to the surrounding tissue, the lower portion may be configured with anchoring members, such as, for example, hooks or barbs (not shown).

Referring again to FIG. 12B, as the balloon 22 expands under the force of the fluid from the fluid pressurizing device, the shape-forming members 24 move with the balloon and force the stent 2 radially outward. As noted above, the shape-forming members 24 are desirably formed of a relatively rigid (or non-compressible) material, at least relative to the stent 2 so that as the balloon 22 expands, the stent 2 is forced outward by the shape-forming members 24 and the stent 2 is expanded to conform generally to the geometry of shape-forming members 24. Hence, the outflow end portion 12 of the stent 2, when expanded, has a generally tri-lobular cross-sectional shape (as best shown in FIG. 6) so as to generally conform to the shape of the aortic root. One advantage of expanding the stent such that it assumes a tri-lobular shape is that the upper end portion 12 can better conform to the natural shape of the surrounding tissue to minimize paravalvular leaks between the stent and the surrounding tissue. Another advantage of expanding the stent to assume a tri-lobular shape is that the stent 2 can form a tight seal with a similarly shaped sewing ring 42 of the prosthetic valve 6 when the valve is deployed within the stent.

FIG. 12D shows a valve component 4 mounted on the distal end of a balloon catheter 34 of a delivery apparatus 32 advancing into position within the base stent 2. In its radially constricted or undeployed state, the coupling stent 8 assumes a conical inward taper in the distal direction. The catheter 34 extends through the valve component 4 and terminates in a distal nose cone 38 which has a conical or bell-shape and covers the tapered distal end of the coupling stent 8. Although not shown, the catheter 34 can extend through an introducing cannula and valve holder.

The illustrated implant procedure therefore involves first delivering and expanding the base stent 2 at the aortic annulus, and then coupling the valve component 4 including the valve 6 thereto. Because the valve 6 in the illustrated embodiment is non-expandable, the entire procedure is typically done using the conventional open-heart technique. However, because the base stent 2 is delivered and implanted by simple expansion, and then the valve component 4 attached thereto by expansion, both without suturing, the entire operation can be completed in much less time than a typical open-heart valve-replacement procedure. This hybrid approach will also be much more comfortable to surgeons familiar with the open-heart procedures and commercially available heart valves.

Moreover, the relatively small change in procedure coupled with the use of proven heart valves should create a much easier regulatory path than strictly expandable, remote procedures. Even if the system must be validated through clinical testing to satisfy the Pre-Market Approval (PMA) process with the FDA (as opposed to a 510 k submission), the acceptance of the valve component 4 at least will be greatly streamlined with a commercial heart valve 6 that is already approved, such as the Magna® Aortic Heart Valve.

As noted above, the prosthetic valve 6 is provided with an expandable coupling mechanism in the form of the coupling stent 8 for securing the valve to the base stent 2. Although the coupling stent 8 is shown, the coupling mechanism may take a variety of different forms, but eliminates the need for connecting sutures and provides a rapid connection means.

Figure 12E:
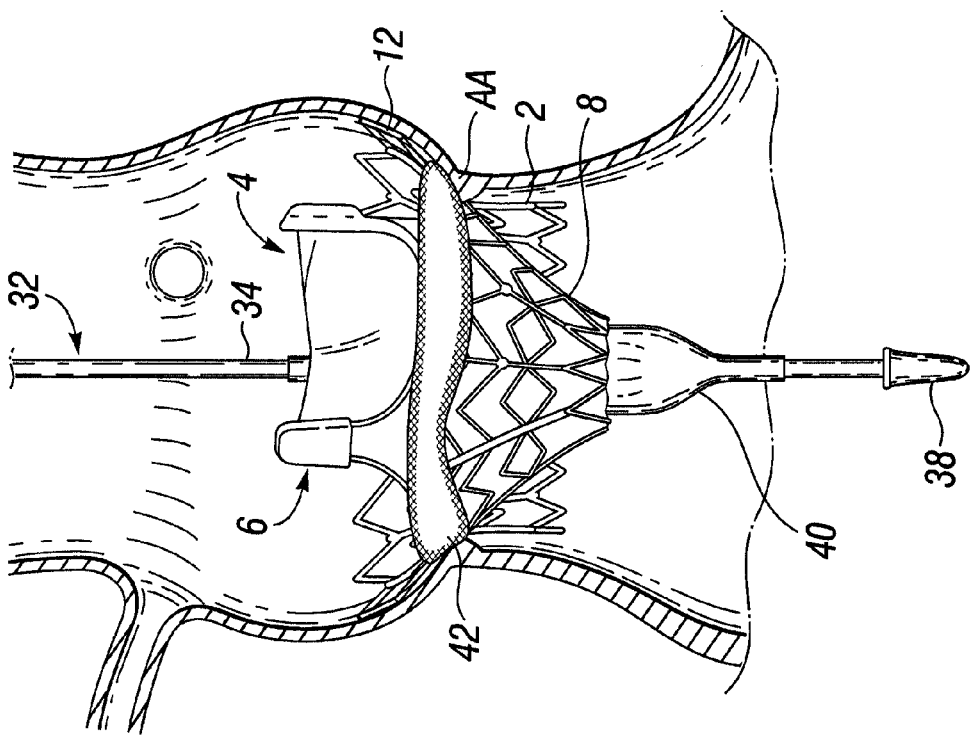

In FIG. 12E the valve component 4 has advanced to a desired implant position at the aortic annulus AA and within the base stent 2. The prosthetic valve 6 may include a suture-permeable ring 42 that desirably seats within the upper portion 12 of the stent 2 adjacent the aortic annulus AA. The balloon catheter 34 has advanced relative to the valve component 4 to displace the nose cone 38 out of engagement with the coupling stent 8. A dilatation balloon 40 on the catheter 4 can be seen just beyond the distal end of the coupling stent 8. As mentioned, the prosthetic valve 6 is desirably a commercially available heart valve having a sewing ring 42, which typically has a tri-lobular shape. Referring to FIG. 28, the valve component 4 desirably is rotationally positioned relative to the base stent 2 such that sinus-shaped sections 42a, 42b, 42c of the ring 42 are aligned within respective sinus-shaped sections 12a, 12b, 12c of the expanded base stent. The ring 42 generally conforms to the tri-lobular shape of the stent upper end portion 12 to form a tight seal between these two components, thereby preventing or at least minimizing paravalvular leakage. Positioning of the valve component in the base stent can be facilitated by aligning the commissure posts 102 of the prosthetic valve (FIG. 18C) with the position markers 190 on the base stent.

FIG. 12F shows the balloon 40 on the catheter 34 inflated to expand and deploy the coupling stent 8 against the base stent 2. The balloon 40 is desirably inflated using controlled, pressurized, sterile physiologic saline. The coupling stent 8 transitions between its conical contracted state and its generally tubular expanded state. Simple interference between the coupling stent 8 and the base stent 2 can be sufficient to anchor the valve component 4 within the base stent, or interacting features such as projections, hooks, barbs, fabric, etc. can be utilized.

Because the base stent 2 expands before the valve component 4 attaches thereto, a higher strength stent (self- or balloon-expandable) configuration may be used. For instance, a relatively robust base stent 2 can be used to push the native leaflets aside, and the absent valve component 4 is not damaged or otherwise adversely affected during the high-pressure base stent deployment. After the base stent 2 deploys in the body channel, the valve component 4 connects thereto by deploying the coupling stent 8, which can be somewhat more lightweight requiring smaller expansion forces. Also, the balloon 40 may have a larger distal expanded end than its proximal expanded end so as to apply more force to the coupling stent 8 than to the prosthetic valve 6. In this way, the prosthetic valve 6 and flexible leaflets therein are not subject to high expansion forces from the balloon 40. Indeed, although balloon deployment is shown, the coupling stent 8 may also be a self-expanding type of stent. In the latter configuration, the nose cone 38 can be adapted to retain the coupling stent 8 in its constricted state prior to positioning the valve component 4 within the base stent 2.

FIG. 12G shows the deflated balloon 40 on the catheter 34 along with the nose cone 38 being removed from within the valve component 4. Finally, FIG. 12H shows the fully deployed prosthetic heart valve system including the valve component 4 coupled to the base stent 2 within the aortic annulus AA. The sewing ring 42 seats within a seating area of the outflow end portion 12 of the base stent. The valve component is further secured against movement or dislodgement toward the left ventricle by virtue of the sewing ring having a greater diameter than the annulus AA and the inflow end portion of the base stent.

As noted above, the base stents described herein could include barbs or other tissue anchors to further secure the stent to the tissue, or to secure the coupling stent 8 to the base stent 2. Further, the barbs could be deployable (e.g., configured to extend or be pushed radially outward) by the expansion of a balloon. Desirably, the coupling stent 8 is covered to promote ingrowth and/or to reduce paravalvular leakage, such as with a Dacron tube or the like.

In an alternative embodiment, the base stent 2 can be delivered and deployed in a minimally invasive, transcatheter technique, such as via the patient's vasculature or using a transapical approach whereby the delivery apparatus is inserted directly into the heart through an incision in the chest. In addition, the valve component can include a radially expandable and collapsible prosthetic valve that can be crimped to a diameter that is small enough to allow the valve component to be delivered and deployed in a minimally invasive, transcatheter technique. In this manner, the base stent and the valve component can be implanted without opening the chest.

Exemplary Delivery Apparatus for Valve Component

FIG. 13 is an exploded view, and FIGS. 14 and 15 are assembled views, of an exemplary delivery apparatus 32 for introducing the prosthetic heart valve of the present invention. Modified components of the delivery apparatus 32 are also shown in FIGS. 16 and 17. The delivery apparatus 32 includes the balloon catheter 34 having the balloon 40 on its distal end and an obturator 54 on a proximal end. The obturator 54 presents a proximal coupling 56 that receives a leur connector or other such fastener such as a Y-fitting 58. The aforementioned nose cone 38 attaches to the distalmost end of the catheter 34.

The catheter 34 and the nose cone 38 pass through a hollow handle 60 having a proximal section 62 and a distal section 64. A distal end of the distal handle section 64 firmly attaches to a hub 66 of a valve holder 68, which in turn attaches to the prosthetic heart valve component 4. Details of the valve holder 68 will be given below with reference to FIGS. 18A-18E.

The two sections 62, 64 of the handle 60 are desirably formed of a rigid material, such as a molded plastic, and coupled to one another to form a relatively rigid and elongated tube for manipulating the prosthetic valve component 4 attached to its distal end. In particular, the distal section 64 may be easily coupled to the holder hub 66 and therefore provide a convenient tool for managing the valve component 4 during pre-surgical rinsing steps. For this purpose, the distal section 64 can have a distal tubular segment 70 that couples to the holder hub 66, and an enlarged proximal segment 72 having an opening on its proximal end that receives a tubular extension 74 of the proximal handle section 62. FIG. 13 shows an O-ring 76 that may be provided on the exterior of the tubular extension 74 for a frictional interference fit to help prevent the two sections from inadvertently disengaging. Although not shown, the distal tubular segment 70 may also have an O-ring for firmly coupling to the holder hub 66, or may be attached with threading or the like. In one embodiment, the balloon 40 on the catheter 34 is packaged within the proximal handle section 62 for protection and ease of handling. Coupling the proximal and distal handle sections 62, 64 therefore "loads" the system 32 such that the balloon catheter 34 may be advanced through the continuous lumen leading to the valve component 4.

FIGS. 16 and 17 illustrate a delivery apparatus 32 similar to that shown in FIG. 14, but with alternative couplers 77 on both the proximal and distal handle sections 62, 64 in the form of cantilevered teeth that snap into complementary recesses formed in the respective receiving apertures. Likewise, threading on the mating parts could also be used, as well as other similar expedients. FIG. 16 shows the balloon 40 inflated to expand the valve component coupling stent 8.

In one embodiment, the prosthetic valve component 4 incorporates bioprosthetic tissue leaflets and is packaged and stored attached to the holder 68 but separate from the other components of the delivery apparatus. Typically, bioprosthetic tissue is packaged and stored in a jar with preservative solution for long shelf life, while the other components are packaged and stored dry.

When assembled as seen in FIGS. 14-16, an elongated lumen (not numbered) extends from the proximal end of the Y-fitting 58 to the interior of the balloon 40. The Y-fitting 58 desirably includes an internally threaded connector 80 for attachment to an insufflation system, or a side port 82 having a leur fitting or similar expedient may be used for insufflation of the balloon 40.

FIGS. 14 and 15 show two longitudinal positions of the catheter 34 and associated structures relative to the handle 60 and its associated structures. In a retracted position shown in FIG. 14, the balloon 40 primarily resides within the distal handle section 64, with a portion projecting between leaflets of the valve component 4. FIG. 14 illustrates the delivery configuration of the delivery apparatus 32, in which the surgeon advances the prosthetic valve component 4 from outside the body into a location adjacent the target annulus. The nose cone 38 extends around and protects a distal end of the undeployed coupling stent 8. This configuration is also seen in FIG. 12D, albeit with the holder 68 removed for clarity. Note the spacing S between the proximal coupling 56 and the proximal end of the handle 60.

As explained above with respect to FIGS. 12A-12H, the surgeon advances the prosthetic valve component 4 into its implantation position, and then advances and inflates the balloon 40. To do so, the operator converts the delivery apparatus 32 from the retracted configuration of FIG. 14 to the deployment configuration of FIG. 15, with the balloon catheter 34 displaced distally as indicated by the arrow 78 to disengage the nose cone 38 from the coupling stent 8. Note that the proximal coupling 56 now contacts the proximal end of the handle 60, eliminating the space S indicated in FIG. 15. Prior to a further description of operation of the delivery apparatus 32, a more detailed explanation of the valve component 4 and valve holder 68 is provided.

Figure 18E:
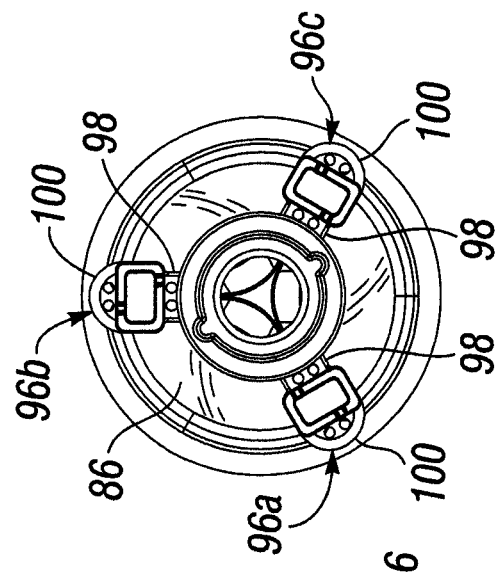
FIGS. 18D and 18E are bottom and top plan views, respectively, of the assembly of FIGS. 18A and 18B.

FIGS. 18A-18E show a number of perspective and other views of the exemplary valve component 4 mounted on the delivery holder 68. As mentioned, the valve component 4 comprises the prosthetic valve 6 having the coupling stent 8 attached to an inflow end thereof. In one embodiment, as discussed above, the prosthetic valve 6 comprises a commercially available, off-the-shelf, non-expandable, non-collapsible commercial prosthetic valve. Any number of prosthetic heart valves can be retrofit to attach the coupling stent 8, and thus be suitable for use with the embodiments disclosed herein. For example, the prosthetic valve 6 may be a mechanical valve or a valve with flexible leaflets, either synthetic or bioprosthetic. In particular embodiments, however, the prosthetic valve 6 includes bioprosthetic tissue leaflets 86 (FIG. 18A). Furthermore, as mentioned above, in a specific implementation the prosthetic valve 6 is desirably a Carpentier-Edwards PERIMOUNT Magna® Aortic Heart Valve (e.g., model 400TFX) available from Edwards Lifesciences of Irvine, Calif.

The coupling stent 8 preferably attaches to the ventricular (or inflow) aspect of the valve's sewing ring 42 during the manufacturing process in a way that preserves the integrity of the sewing ring and prevents reduction of the valve's effective orifice area (EOA). Desirably, the coupling stent 8 is continuously sutured to sewing ring 42 in a manner that maintains the outer contours of the sewing ring. Sutures may be passed through apertures or eyelets in the stent skeleton, or through a cloth covering that in turn is sewn to the skeleton. Other connection solutions include prongs or hooks extending inward from the stent, ties, Velcro, snaps, adhesives, etc. Alternatively, the coupling stent 8 may be more rigidly connected to rigid components within the prosthetic valve 6. During implant, therefore, the surgeon can seat the sewing ring 42 against the annulus in accordance with a conventional surgery. This gives the surgeon familiar tactile feedback to ensure that the proper patient-prosthesis match has been achieved. Moreover, placement of the sewing ring 42 against the outflow side of the annulus helps reduce the probability of migration of the valve component 4 toward the ventricle.

The coupling stent 8 may be a pre-crimped, tapered, 316 L stainless steel balloon-expandable stent, desirably is covered by a polyester skirt 88 to help seal against paravalvular leakage and promote tissue ingrowth once implanted within the base stent 2 (see FIG. 18B). The coupling stent 8 transitions between the tapered constricted shape of FIGS. 18A-18E to its flared expanded shape shown in FIG. 12F, and also in FIG. 16.

The coupling stent 8 desirably comprises a plurality of sawtooth-shaped or otherwise angled, serpentine or web-like struts 90 connected to three generally axially-extending posts 92. As will be seen below, the posts 92 desirably feature a series of evenly spaced apertures to which sutures holding the polyester skirt 88 in place may be anchored. As seen best in FIG. 12F, the stent 8 when expanded conforms closely against the inner surface of the base stent 2. Anchoring devices such as barbs or other protruberances from the coupling stent 8 may be provided to enhance the frictional hold between the coupling stent and the base stent 2.

It should be understood that the particular configuration of the coupling stent, whether possessing straight or curvilinear struts 90, may be modified as needed. There are numerous stent designs, as described below with reference to FIGS. 19-24 any of which potentially may be suitable Likewise, although the preferred embodiment incorporates a balloon-expandable coupling stent 8, a self-expanding stent could be substituted with certain modifications, primarily to the delivery system. The same flexibility and design of course applies to the base stent 2. In certain embodiments, both the base stent 2 and the coupling stent 8 are desirably plastically-expandable to provide a firmer anchor for the valve 6; first to the annulus with or without native leaflets, and then between the two stents. The stents may be expanded using a balloon or mechanical expander as described above.

Still with reference to FIGS. 18A-18E, the holder 68 comprises the aforementioned proximal hub 66 and a thinner distal extension 94 thereof forming a central portion of the holder. Three legs 96a, 96b, 96c circumferentially equidistantly spaced around the central extension 94 and projecting radially outward therefrom comprise inner struts 98 and outer commissure rests 100. The prosthetic valve 6 preferably includes a plurality, typically three, commissures posts 102 that project in an outflow direction and support the leaflets 86. Although not shown, the commissure rests 100 preferably incorporate depressions into which fit the tips of the commissures posts 102.

In one embodiment, the holder 68 is formed of a rigid polymer such as acetal homopolymer or polypropylene that is transparent to increase visibility of an implant procedure. As best seen in FIG. 18E, the holder 68 defines openings between the legs 96a, 96b, 96c to provide a surgeon good visibility of the valve leaflets 86, and the transparency of the legs further facilitates visibility and permits transmission of light therethrough to minimize shadows. Although not described in detail herein, FIG. 18E also illustrate a series of through holes in the legs 96a, 96b, 96c permitting connecting sutures to be passed through fabric in the prosthetic valve 6 and across a cutting guide in each leg. As is known in the art, severing a middle length of suture that is connected to the holder 68 and passes through the valve permits the holder to be pulled free from the valve when desired.

Embodiments of Coupling Stent

Figure 18C:
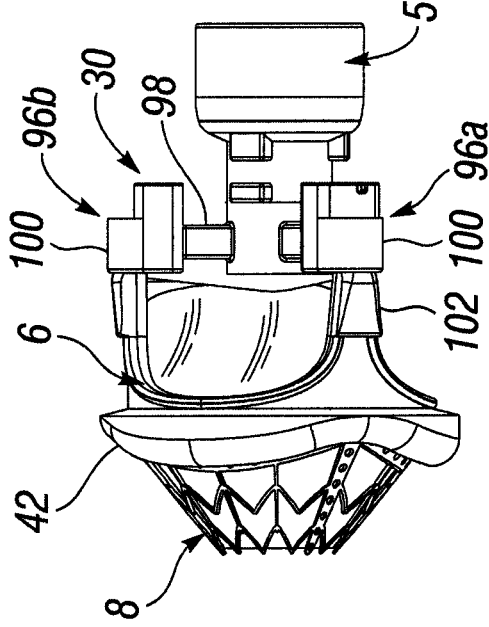
FIG. 18C is a side elevational view of the assembly of FIGS. 18A and 18B.
Figure 18D:
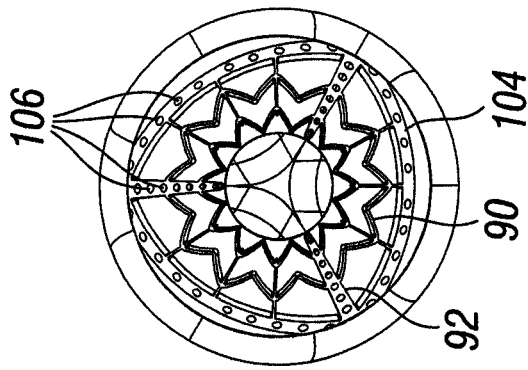

FIGS. 18C and 18D illustrate a somewhat modified coupling stent 8 from that shown in FIGS. 18A and 18B, wherein the struts 90 and axially-extending posts 92 are better defined. Specifically, the posts 92 are somewhat wider and more robust than the struts 90, as the latter provide the stent 8 with the ability to expand from the conical shape shown to a more tubular configuration. Also, a generally circular reinforcing ring 104 abuts the valve sewing ring 42. Both the posts 92 and the ring 104 further include a series of through holes 106 that may be used to secure the polyester skirt 88 to the stent 8 using sutures or the like. A number of variants of the coupling stent 8 are also described below.

Figure 19A:
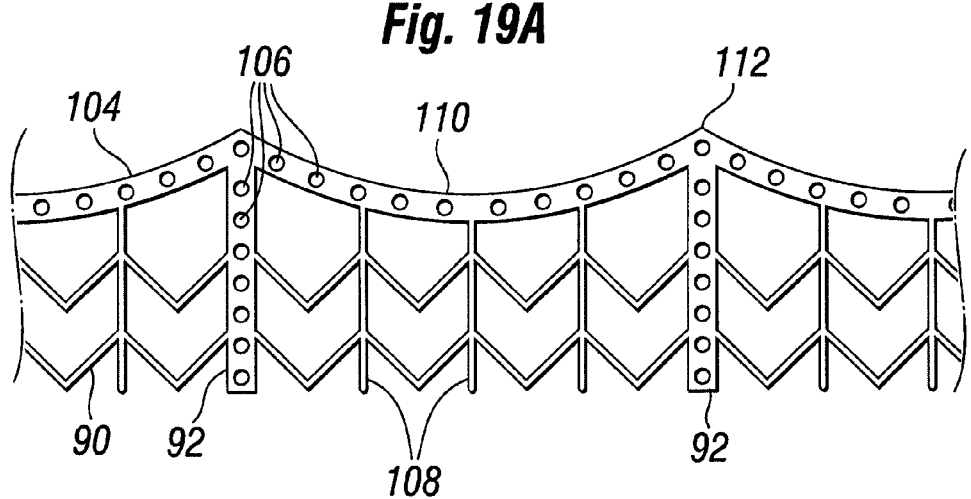
FIGS. 19A-19B illustrate an exemplary coupling stent in both a flat configuration (19A) and a tubular expanded configuration (19B).
Figure 19B:
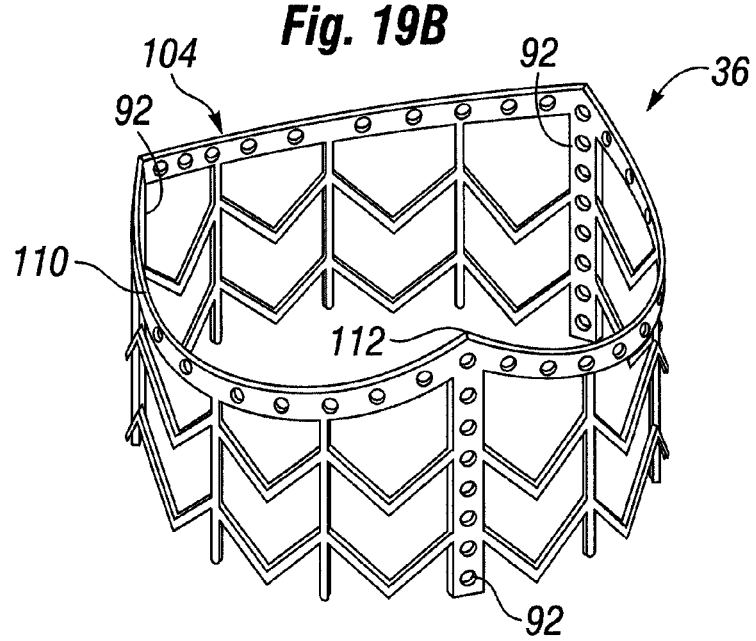

FIGS. 19A-19B illustrate the exemplary coupling stent 8 in both a flat configuration (19A) and a tubular configuration (19B) that is generally the expanded shape. As mentioned, the web-like struts 90 and a reinforcing ring 104 connect three generally axially-extending posts 92. A plurality of evenly spaced apertures 106 provide anchors for holding the polyester skirt 88 (see FIG. 18B) in place. In the illustrated embodiment, the web-like struts 90 also include a series of axially-extending struts 108. An upper end of the coupling stent 8 that connects to the sewing ring of the valve and is defined by the reinforcing ring 104 follows an undulating path with alternating arcuate troughs 110 and pointed peaks 112. As best shown in FIG. 18B, the exemplary prosthetic valve 6 has an undulating sewing ring 42 to which the upper end of the coupling stent 8 conforms. Of course, if the sewing ring of the prosthetic valve is planar, then the upper end of the coupling stent 8 can be planar. It should be noted also that the tubular version of FIG. 19B is an illustration of an expanded configuration, although the balloon 40 may over-expand the free (lower) end of the stent 8 such that it ends up being slightly conical.

Figure 20A:
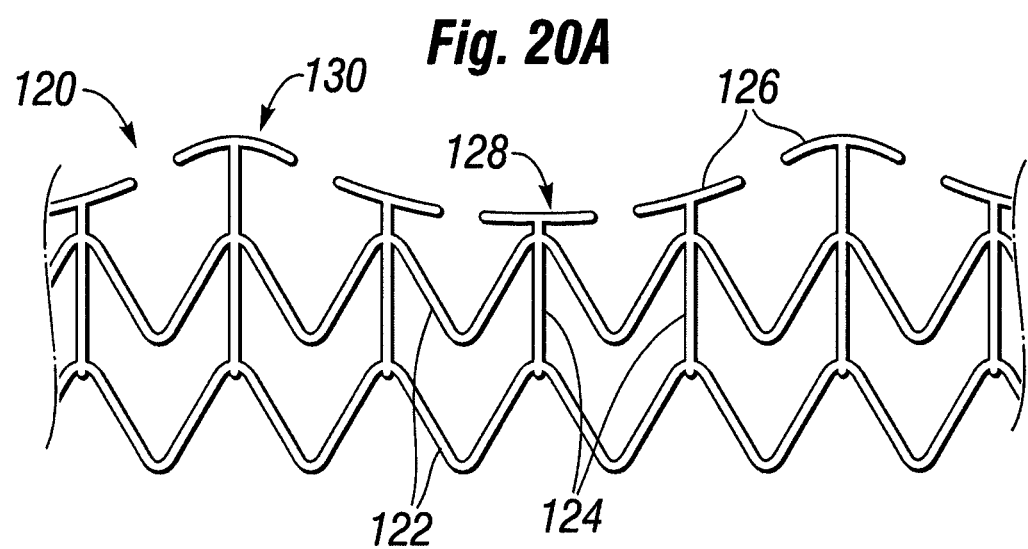
FIGS. 20A-20B illustrate an alternative coupling stent having a discontinuous upper end in both flat and tubular expanded configurations.
Figure 20B:
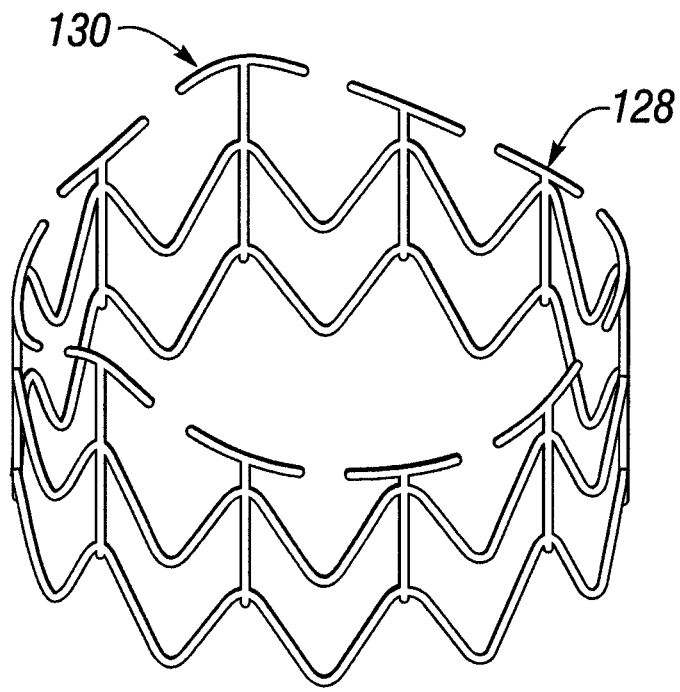

FIGS. 20A and 20B show an alternative coupling stent 120, again in flattened and tubular configurations, respectively. As with the first embodiment, the coupling stent 120 includes web-like struts 122 extending between a series of axially-extending struts 124. In this embodiment, all of the axially-extending struts 124 are substantially the same thin cross-sectional size. The upper or connected end of the stent 120 again can include a reinforcing ring 126, although this version is interrupted with a series of short lengths separated by gaps. The upper end defines a plurality of alternating troughs 128 and peaks 130, with lengths of the reinforcing ring 126 defining the peaks. The axially-extending struts 124 are in-phase with the scalloped shape of the upper end of the stent 120, and coincide with the peaks and the middle of the troughs.

The gaps between the lengths making up the reinforcing ring 126 permit the stent 120 to be matched with a number of different sized prosthetic valves 6. That is, the majority of the stent 120 is expandable having a variable diameter, and providing gaps in the reinforcing ring 126 allows the upper end to also have a variable diameter so that it can be shaped to match the size of the corresponding sewing ring of the selected valve. This reduces manufacturing costs as correspondingly sized stents need not be used for each different sized valve.

FIG. 21 is a plan view of a still further alternative coupling stent 132 that is very similar to the coupling stent 120, including web-like struts 134 connected between a series of axially-extending struts 136, and the upper end is defined by a reinforcing ring 138 formed by a series of short lengths of struts. In contrast to the embodiment of FIGS. 20A and 20B, the peaks of the undulating upper end have gaps as opposed to struts. Another way to express this is that the axially-extending struts 136 are out-of-phase with the scalloped shape of the upper end of the stent 132, and do not correspond to the peaks and the middle of the troughs.

FIG. 22 illustrates an exemplary coupling stent 140 again having the expandable struts 142 between the axially-extending struts 144, and an upper reinforcing ring 146. The axially-extending struts 144 are in-phase with peaks and troughs of the upper end of the stent. The reinforcing ring 146 is a cross between the earlier-described such rings as it is continuous around its periphery but also has a variable diameter. That is, the ring 146 comprises a series of lengths of struts 148 of fixed length connected by thinner bridge portions 150 of variable length. The bridge portions 150 are each formed with a radius so that they can be either straightened (lengthened) or bent more (compressed). A series of apertures 152 can be formed in an upper end of the stent 140 provide anchor points for sutures or other attachment means when securing the stent to the sewing ring of the corresponding prosthetic valve.

In FIG. 23, an alternative coupling stent 154 is identical to the stent 140 of FIG. 22, although the axially-extending struts 156 are out-of-phase with the peaks and troughs of the undulating upper end.

FIG. 24 shows a still further variation on a coupling stent 160, which has a series of expandable struts 162 connecting axially-extending struts 164. As with the version shown in FIGS. 19A and 19B, the web-like struts 162 also include a series of axially-extending struts 166, although these are thinner than the main axial struts 164. A reinforcing ring 168 is also thicker than the web-like struts 162, and features one or more gaps 170 in each trough such that the ring is discontinuous and expandable. Barbs 172, 174 on the axially extending struts 164, 166 may be utilized to enhance retention between the coupling stent 160 and a base stent with which it cooperates.

As mentioned above, the two-component valve systems described herein utilize an outer or base stent (such as base stent 2) and a valve component having an inner or valve stent (such as coupling stent 8). The valve and its stent advance into the lumen of the pre-anchored outer stent and the valve stent expands to join the two stents and anchor the valve into its implant position. It is important that the inner stent and outer stent be correctly positioned both circumferentially and axially to minimize subsequent relative motion between the stents. Indeed, for the primary application of an aortic valve replacement, the circumferential position of the commissures of the valve relative to the native commissures is very important. A number of variations of coupling stent that attach to the valve component have been shown and described above. FIGS. 25-27 illustrate exemplary base stents and cooperation between the two stents.

Embodiments of Base Stent

FIGS. 25A and 25B show an exemplary embodiment of a base stent 180 comprising a plurality of radially-expandable struts 182 extending between a plurality of generally axially-extending struts 184. In the illustrated embodiment the struts 182 form chevron patterns between the struts 184, although other configurations such as serpentine or diamond-shaped could also be used. The top and bottom rows of the radially-expandable struts 182 are arranged in a position so as to form a plurality of triangular peaks 186 and troughs 188. The axial struts 184 are in-phase with the troughs 188. Although FIG. 25B depicts the base stent 180 as having a cylindrical expanded shape, the stent 180 can be expanded to have the shape shown in FIGS. 5 and 6 using one of the expansion devices described above.

The flattened view of FIG. 25A shows four axial projections 190 that each extend upward from one of the axial struts 184. Although four projections 190 are shown, the exemplary base stent 180 desirably has three evenly circumferentially spaced projections (i.e., spaced 120 degrees apart from each other), as seen around the periphery in the tubular version of FIG. 25B, providing location markers for the base stent. These markers thus make it easier for the surgeon to orient the stent 180 such that the markers align with the native commissures. Furthermore, as the valve component advances to within the base stent 180, the visible projections 190 provide reference marks such that the inner stent can be properly oriented within the base stent. In this regard the projections 190 may be differently colored than the rest of the stent 180. If the base stent and valve component are implanted in a surgical technique, as described in detail above, the surgeon can have direct visual access (as opposed to using imaging techniques) to facilitate alignment of the base stent relative to the annulus and alignment of the valve component relative to the base stent. If desired, the projections can have radiopaque indicators thereon. The length of the projections 190 above the upper row of middle struts 182 may also be calibrated to help the surgeon axially position the stent 180. For example, the distance from the tips of the projections 190 to the level of the native annulus could be determined, and the projections 190 located at a particular anatomical landmark such as just below the level of the coronary ostia.

When the base stent is expanded in the manner shown in FIG. 28, each projection 190 is located at the juncture of two sinus shaped sections 12a, 12b, 12c of the base stent. During delivery of the base stent, the projections 190 are aligned with the native commissures and the base stent is expanded such that the sinus shaped sections 12a, 12b, 12c are aligned within respective sinuses of the aortic root. Subsequently, the valve component can be positioned at its target location relative to the expanded base stent by aligning the commissure posts 102 of the valve component with the projections 190 such that the sinus shaped sections of the sewing ring 42a, 42b, 42c are aligned within respective sinus shaped sections 12a, 12b, 12c of the base stent.

Referring again to FIG. 25A, an undulating dashed line 192 represents the upper end of the inner or coupling stent 140, which is shown in phantom superimposed over the base stent 180. As such, the dashed line 192 also represents an undulating sewing ring, and it bears repeating that the sewing ring could be planar such that the upper end of the coupling stent is also planar. The coupling stent 140 includes axially-extending struts that are in-phase with the respective peaks and troughs of the scalloped upper end of the stent. In the illustrated combination, the peaks of the scalloped upper end of the coupling stent (dashed line 192) correspond rotationally (are in-phase) with the axial struts 184 that have the projections 190. Therefore, because the coupling stent 140 axial struts are in-phase with the peaks of the upper end thereof, they are also in-phase with the axial struts 184 of the base stent 180. Conversely, a coupling stent may have axial struts out-of-phase with peaks of the upper end thereof, in which case the respective axial struts of the two stents are also out-of-phase.

FIG. 26 shows an alternative base stent 200 that generally has the same components as the base stent 180 of FIG. 25A, but the axial struts 184 extend between the peaks 186 of the outer rows of middle struts 182. In the earlier embodiment, the axial struts 184 extended between the troughs 188. The coupling stent 154 of FIG. 23 is shown in phantom superimposed over the base stent 200 to illustrate how the axial struts of the two stents are now out-of-phase to increase interlocking therebetween.

The stent 200 also exhibits different rows of middle struts 182. Specifically, a first row 202a defines V's having relatively shallow angles, a second row 202b defines V's with medium angles, and a third row 202c defined V's with more acute angles. The different angles formed by the middle struts 182 in these rows helps shape the stent into a conical form when expanded. There is, the struts in the third row 202c which is farthest from the prosthetic valve have the greatest capacity for expansion to accommodate the transition from a collapsed conical shape of the stent to an expanded tubular shape.

FIG. 29 shows an alternative base stent 220 that is similar to the base stent 2 described above, except that the base stent 220 has a plurality of positional markers 222. The stent 220 desirably has three equally spaced markers 222 that are aligned with the native commissures when the stent is deployed in the native annulus. Each marker 222 has an axially extending lower portion 224 and a radially extending upper portion 226 that projects outwardly beyond the outer diameter of the stent. The upper portions 226 are spaced above the outflow end of the stent a predetermined distance such that they can contact the tissue above the annulus AA (FIG. 12A) in the aortic root during positioning of the stent so as to provide tactile feedback to the surgeon to help position the stent axially relative to the annulus AA. In a specific implementation, the base stent is partially expanded to diameter large enough such that the upper portions 226 of the position markers can contact the aortic root to assist in positioning the stent, yet the partially expanded stent can still be moved rotationally and axially relative to the annulus. When the surgeon locates the desired axial and rotational position of the stent, the stent is fully expanded to its functional size engaging the surrounding tissue.

Those of skill in the art will understand that there are many ways to increase retention between the two stents. For example, the peaks and troughs of the web-like expandable struts on the two stents could be oriented out-of-phase or in-phase. In one embodiment the peaks and troughs of the two stents are out of phase so that expansion of the inner stent causes its peaks to deform outwardly into the troughs of the outer stent, and thereby provide interlocking structure therebetween. The variations described above provide a number of permutations of this cooperation.

Additionally, axial projections on one or both of stents could be bent to provide an interference with the other stent. For example, the lower ends of the axial struts 108 in the stent 8 shown in FIG. 19A could be bent outward by expansion of a non-uniform shaped balloon such that they extend in voids within the outer stent Likewise, the embodiment of FIG. 24 illustrates barbs 172, 174 that can be bent outward into interference with the corresponding base stent. Strut ends or barbs that transition from one position to another to increase retention between the two stents can be actuated by mechanical bending, such as with a balloon, or through an automatic shape change upon installation within the body. Namely, some shape memory alloys such as Nitinol can be designed to undergo a shape change upon a temperature change, such that they assume a first shape at room temperature, and a second shape at body temperature.

FIG. 27 illustrates a simplified means for increasing retention between the two stents. An inner valve stent 210 fits within an outer base stent 212 such that a lower end 214 thereof extends below the outer stent. By over-expansion of the balloon within the inner stent 210, the lower end 214 is caused to bend or wrap outward to resist relative upward movement of the inner stent within the outer stent.

In another advantageous feature, the two-component valve system illustrated in the preceding figures provides a device and method that substantially reduces the time of the surgical procedure as compared with replacement valves that are sutured to the tissue after removing the native leaflets. For example, the stent 2 of FIGS. 5-6 may be deployed quickly and the valve component 4 may also be quickly attached to the stent. This reduces the time required on extracorporeal circulation and thereby substantially reduces the risk to the patient.

In addition to speeding up the implant process, the present technology having the pre-anchored stent, within which the valve and its stent mount, permits the annulus to be expanded to accommodate a larger valve than otherwise would be possible. In particular, clinical research has shown that the left ventricular outflow tract (LVOT) can be expanded between 3-12 mm by a balloon-expandable stent. This expansion of the annulus creates an opportunity to increase the size of a surgically implanted prosthetic valve. The present technology employs a balloon-expandable base stent, and a balloon-expandable valve stent. The combination of these two stents permits expansion of the LVOT at and just below the aortic annulus, at the inflow end of the prosthetic valve. The interference fit created between the outside of the base stent and the LVOT secures the valve without pledgets or sutures taking up space, thereby allowing for placement of the maximum possible valve size. A larger valve size than would otherwise be available with conventional surgery enhances volumetric blood flow and reduces the pressure gradient through the valve.

It will be appreciated by those skilled in the art that embodiments of the present technology provide important new devices and methods wherein a valve may be securely anchored to a body lumen in a quick and efficient manner. Embodiments of the present technology provide a means for implanting a prosthetic valve in a surgical procedure without requiring the surgeon to suture the valve to the tissue. Accordingly, the surgical procedure time can be substantially decreased. Furthermore, in addition to providing a base stent for the valve, the base stent may be used to maintain the native valve in a dilated condition. As a result, in some cases it is not necessary for the surgeon to remove the native leaflets, thereby further reducing the procedure time.

It will also be appreciated that the present technology provides an improved system wherein a failed prosthetic valve member may be replaced in a more quick and efficient manner. More particularly, it is not necessary to cut any sutures in order to remove the valve. Rather, the valve member may be disconnected from the base stent and a new valve member may be connected in its place. This is an important advantage when using biological tissue valves or other valves having limited design lives.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a prosthetic heart valve system at an aortic heart valve annulus, comprising:

advancing a base stent to an implant position adjacent an aortic heart valve annulus;

radially expanding the base stent so as to anchor the base stent to the aortic heart valve annulus, the expanded base stent having an outflow end portion and an inflow end portion, at least a portion of the outflow end portion having a three-lobed cross-sectional profile with three outwardly-projecting lobes intermediate three regions of lesser radial dimension;

providing a prosthetic valve having a support frame surrounding an orifice including a non-expandable, non-collapsible valve stent coupled to leaflets that coapt within the orifice and form the occluding surfaces of the prosthetic valve, the prosthetic valve further having a coupling stent connected to and extending from an inflow end of the valve stent;

advancing the prosthetic valve into the outflow end portion of the base stent; and radially expanding the coupling stent to an expanded state so as to anchor the prosthetic valve to the base stent.

2. The method of claim 1, wherein the support frame has a diameter that is less than a diameter of the inflow end portion of the base stent.

3. The method of claim 1, wherein the prosthetic valve has a sewing ring with a three-lobed shape, and the step of anchoring the prosthetic valve comprises positioning the three lobes of the sewing ring within the three outward lobes of the outflow end portion of the base stent.

4. The method of claim 1, wherein the base stent is anchored to the aortic heart valve annulus such that the inflow end portion extends into the adjacent left ventricle and the three outward lobes of the outflow end portion extend into respective sinuses of Valsalva of the adjacent ascending aorta.

5. The heart valve system of claim 4, wherein the prosthetic valve has a sewing ring that seats against the portion of the base stent having the three-lobed cross-sectional profile at a location just above the aortic annulus, and wherein the step of anchoring the prosthetic valve comprises radially expanding the coupling stent to an expanded state extending into and engaging the inflow end portion of the base stent.

6. The method of claim 1, wherein the base stent is plastically expandable.

7. The method of claim 6, wherein prior to advancing the base stent to the implant position, the base stent is mounted in a radially compressed state on an outer mounting surface of an expansion device, and the step of expanding the base stent comprises expanding the expansion device to effect expansion of the base stent, wherein expansion of the expansion device causes at least a portion of the outflow end portion to assume the three-lobed cross-sectional profile.

8. The method of claim 7, wherein the expansion device comprises a plurality of shape-forming members having respective outer surfaces collectively defining the outer mounting surface, the shape-forming members being moveable radially outward from each other to expand the base stent when the expansion device is expanded to its expanded configuration.

9. The method of claim 8, wherein the expansion device further comprises an inflatable balloon on which the shape-forming members are mounted.

10. The method of claim 8, wherein the each shape-forming member is configured to contact adjacent shape-forming members on two adjacent sides to form the outer mounting surface of the expandable device, and when the shape-forming members move radially outward from each other the adjacent sides thereof separate.

11. A method of implanting a prosthetic heart valve system at an aortic heart valve annulus, comprising:

advancing a plastically expandable base stent on an outer mounting surface of an expansion device of a catheter to an implant position adjacent an aortic heart valve annulus;

radially expanding the expansion device to expand the base stent and anchor the base stent to the aortic heart valve annulus, the expanded base stent having an outflow end portion and an inflow end portion, wherein the step of expanding the expansion device causes the outer mounting surface to expand unevenly and force the plastically expandable outflow end portion of the base stent to assume a three-lobed cross-sectional profile with three outwardly-projecting lobes intermediate three regions of lesser radial dimension;

providing a prosthetic valve having a support frame surrounding an orifice including a non-expandable, non-collapsible valve stent coupled to leaflets that coapt within the orifice and form the occluding surfaces of the prosthetic valve, the prosthetic valve further having a plastically expandable coupling stent connected to and extending from an inflow end of the valve stent;

advancing the prosthetic valve such that the support frame is located within the outflow end portion of the base stent; and radially expanding the coupling stent to an expanded state so as to anchor the prosthetic valve to the inflow end portion of the base stent.

12. The method of claim 11, wherein the support frame attaches to a peripheral sewing ring that has a diameter that is greater than a diameter of the inflow end portion of the base stent such that the support frame is prevented from advancing into the inflow end portion.

13. The method of claim 11, wherein the prosthetic valve has a sewing ring with a three-lobed shape which conforms to the three outward lobes of the outflow end portion of the base stent.

14. The method of claim 11, wherein the base stent is anchored to the aortic heart valve annulus such that the inflow end portion extends into the adjacent left ventricle and the three outward lobes of the outflow end portion extend into respective sinuses of Valsalva of the adjacent ascending aorta.

15. The heart valve system of claim 14, wherein the prosthetic valve has a sewing ring that seats against the portion of the base stent having the three-lobed cross-sectional profile at a location just above the aortic annulus.

16. The method of claim 11, wherein the expansion device comprises a plurality of shape-forming members having respective outer surfaces collectively defining the outer mounting surface, the shape-forming members being moveable radially outward from each other to expand the base stent when the expansion device is expanded to its expanded configuration.

17. The method of claim 16, wherein the expansion device further comprises an inflatable balloon on which the shape-forming members are mounted.

18. The method of claim 17, wherein there are three solid shape-forming members mounted on the balloon.

19. The method of claim 16, wherein the each shape-forming member is configured to contact adjacent shape-forming members on two adjacent sides to form the outer mounting surface of the expandable device, and when the shape-forming members move radially outward from each other the adjacent sides thereof separate.

20. The method of claim 11, wherein the step of advancing the prosthetic valve comprises advancing the prosthetic valve on a catheter with the coupling stent carried in a contracted state on a balloon of the catheter.

* * * * *